US010227580B2

(12) United States Patent
Leland

(10) Patent No.: US 10,227,580 B2
(45) Date of Patent: Mar. 12, 2019

(54) METHOD AND DEVICE FOR PLANKTON SEPARATION

(71) Applicant: Nancy Leland, North Andover, MA (US)

(72) Inventor: Nancy Leland, North Andover, MA (US)

(*) Notice: Subject to any disclaimer, the term of this patent is extended or adjusted under 35 U.S.C. 154(b) by 93 days.

(21) Appl. No.: 15/345,823

(22) Filed: Nov. 8, 2016

(65) Prior Publication Data

US 2017/0067043 A1   Mar. 9, 2017

Related U.S. Application Data

(63) Continuation of application No. 14/615,110, filed on Feb. 5, 2015, now Pat. No. 9,540,632.

(60) Provisional application No. 61/936,698, filed on Feb. 6, 2014.

(51) Int. Cl.

| C12N 1/02 | (2006.01) |
|---|---|
| C12N 13/00 | (2006.01) |
| C12M 1/00 | (2006.01) |
| C12N 1/10 | (2006.01) |
| C12N 1/12 | (2006.01) |
| C12N 1/20 | (2006.01) |

(52) U.S. Cl.
CPC ............. *C12N 13/00* (2013.01); *C12M 47/02* (2013.01); *C12N 1/02* (2013.01); *C12N 1/10* (2013.01); *C12N 1/12* (2013.01); *C12N 1/20* (2013.01)

(58) Field of Classification Search
CPC . A01G 33/00; C12N 1/02; C12N 1/12; C12N 1/10; C12N 1/20; C12M 47/02; C02F 2103/007; C02F 3/322; A01K 61/20; A01K 61/90

USPC .......................... 210/767; 47/1.4; 73/170.29
See application file for complete search history.

(56) References Cited

U.S. PATENT DOCUMENTS

| 3,838,793 A | 10/1974 | Rochette |
|---|---|---|
| 5,713,303 A | 2/1998 | Willinsky et al. |
| 6,123,858 A | 9/2000 | Manz |
| 7,000,567 B1 | 2/2006 | Hsiao |
| 7,201,114 B2 | 4/2007 | Hsiao |
| 7,820,025 B2 | 10/2010 | Ciampi et al. |

(Continued)

FOREIGN PATENT DOCUMENTS

| CN | 201803883 U | 4/2011 |
|---|---|---|
| CN | 102422828 A | 4/2012 |
| JP | 2001161207 A | 6/2001 |

OTHER PUBLICATIONS

Johnson, Microcystins in New Hampshire Lakes and Bioaccumulation in Zooplankton, Thesis, University of New Hampshire, pp. 1-108 (Year: 1999).*

(Continued)

*Primary Examiner* — Claire A Norris
(74) *Attorney, Agent, or Firm* — Hamilton, Brook, Simth & Reynolds, P.C.

(57) ABSTRACT

Methods, devices and kits for the physical separation of plankton into its component parts utilizing phototactic behavior are described. The methods utilize positive phototactic behavior and negative contrast orientation of the zooplankton for maximal in situ separation of phytoplankton and zooplankton for use in further studies and evaluation of separation efficiency. The devices provide effective conditions for use in the separation of plankton into component parts.

14 Claims, 19 Drawing Sheets

(56) References Cited

U.S. PATENT DOCUMENTS

| | | | |
|---|---|---|---|
| 8,580,560 | B1 | 11/2013 | Ellis et al. |
| 9,540,632 | B2 | 1/2017 | Leland |
| 2003/0143752 | A1 | 7/2003 | Feldsine et al. |
| 2012/0125836 | A1 | 5/2012 | Hintz et al. |
| 2013/0233779 | A1 | 9/2013 | Farrish |
| 2016/0312173 | A1 | 10/2016 | Leland |

OTHER PUBLICATIONS

Buchanan, C., et al., "A laboratory method for studying zooplankton swimming behaviors," *Hydrobiologia*, 94: 77-89 (1982).

Forward, R., Jr., "Diel Vertical Migration: Zooplankton Photobiology and Behaviour," *Oceanography Marine Biology Annual Review*, 26: 361-393 (1988).

Graham, J., et al., "Guidelines for Design and Sampling for Cyanobacterial Toxin and Taste-and-Odor Studies in Lakes and Reservoirs," *Scientific Investigations Report 2008-5038 of the U.S. Department of the Interior and U.S. Geological Survey*.

Ringelberg, J., "An account of a preliminary mechanistic model of swimming behaviour in *Daphnia*: its use in understanding diel vertical migration," *Hydrobiologia*, 307: 161-165 (1995).

Ringelberg, J., et al., "Contrast Orientation in Daphnia Magna and its Significance for Vertical Plane Orientation in the Pelagic Biotope in General," *Netherlands Journal of Zoology*, 25(4): 454-475 (1975).

Ringelberg, J., "Changes in Light Intensity and Diel Vertical Migration: A Comparison of Marine and Freshwater Environments," *Journal of Marine Biology Association U.K.*, 75: 15-25 (1995).

Ringelberg, J., "The Positively Phototactic Reaction of Daphnia Magna Straus: A Contribution to the Understanding of Diurnal Vertical Migration," *Netherlands Journal of Sea Research*, 2(3): 319-406 (1964).

Schallek, W., "The Vertical Migration of the Copepod Acartia Tonsa Under Controlled Illumination," *Biological Laboratories, Harvard University and the Woods Hole Oceanographic Institution*, pp. 112-126 (1942).

"Scientific Assessment of Freshwater Harmful Algal Blooms," *Interagency Working Group on Harmful Algal Blooms, Hypoxia, and Human Health* (2008).

United States Environmental Protection Agency (2012) "Cyanobacteria and Cyanotoxins: Information for Drinking Water Systems," (EPA-810F11001).

Capron, S. "Occurrence of Microcystins Produced by Microcystis Aeruginosa (Blue-Green Algae) and Accumulation in Zooplankton," Thesis, University of New Hampshire (1995).

Johnson, K., "Microcystins in New Hampshire Lakes and Bioaccumulation in Zooplankton," Thesis, University of New Hampshire (1999).

Hathaway, Richard., II., "Bioaccumulation of Microcystin in Crayfish and Mussels Within New Hampshire Lakes and Their Potential as Biomonitors," Thesis, B.A. State of University of New York at Plattsburgh (2001).

Cai, Haiyuan et al., "Bacterial Community Composition of Size-Fractioned Aggregates within the Phycosphere of Cyanobacterial Blooms in a Eutrophic Freshwater Lake," *Plos One*, 9(8): 1-11 (Aug. 2014).

Cyanobacteria (Blue-green Algae) Guidance for Vermont Communities, Vermont Department of Health, 40 pages (Aug. 2015).

Kromkamp, Jacco C. and Luuc R. Mur, "Buoyant density changes in the cyanobacterium *Microcystis aeruginosa* due to changes in the cellular carbohydrate content," *FEMS Microbiology Letters*, 25: 105-109 (1984).

Kromkamp, Jacco C. and Anthony E. Walsby, "A computer model of buoyancy and vertical migration in cyanobacteria," *Journal of Plankton Research*, 12(1): 161-183 (1990).

Nakamura, Takahiko et al., "Flotation and Sedimentation of a Single *Microcystis* Floc Collected from Surface Bloom," *Wat. Res.*, 27(6): 979-983 (1993).

Oliver, Roderick Lewis, "Floating and Sinking in Gas-vacuolate Cyanobacteria," *Journal of Phycology*, 30: 161-173 (1994).

Reynolds, Colin S. et al. "Cyanobacterial dominance: the role of buoyancy regulation in dynamic lake environments," *New Zealand Journal of Marine and Freshwater Research*, 21: 379-390 (1987).

Rowe, M.D. et al., "Vertical distribution of buoyant *Microcystis* blooms in a Lagrangian particle tracking model for short-term forecasts in Lake Erie," *Journal of Geophysical Research: Oceans. Research Article*, 10.1002/2016JC011720: pp. 1-19 (2016).

Thomas, R.H. and A.E. Walsby, "Buoyancy Regulation in a Strain of Microcystis," *Journal of General Microbiology*, 131: 799-809 (1985).

Van Rijn, Jaap and Moshe Shilo, "Carbohydrate fluctuations, gas vacuolation, and vertical migration of scum-forming cyanobacteria in fishponds," *Limnol. Oceanogr.*, 30(6): 1219-1228 (1985).

Office Action, U.S. Appl. No. 15/152,359, filed May 11, 2016, entitled "Method and Device for Plankton Separation", Date of Communication: Jun. 26, 2018.

Notice of Allowance, U.S. Appl. No. 15/152,359, filed May 11, 2016, entitled "Method and Device for Plankton Separation", dated Nov. 1, 2018.

* cited by examiner

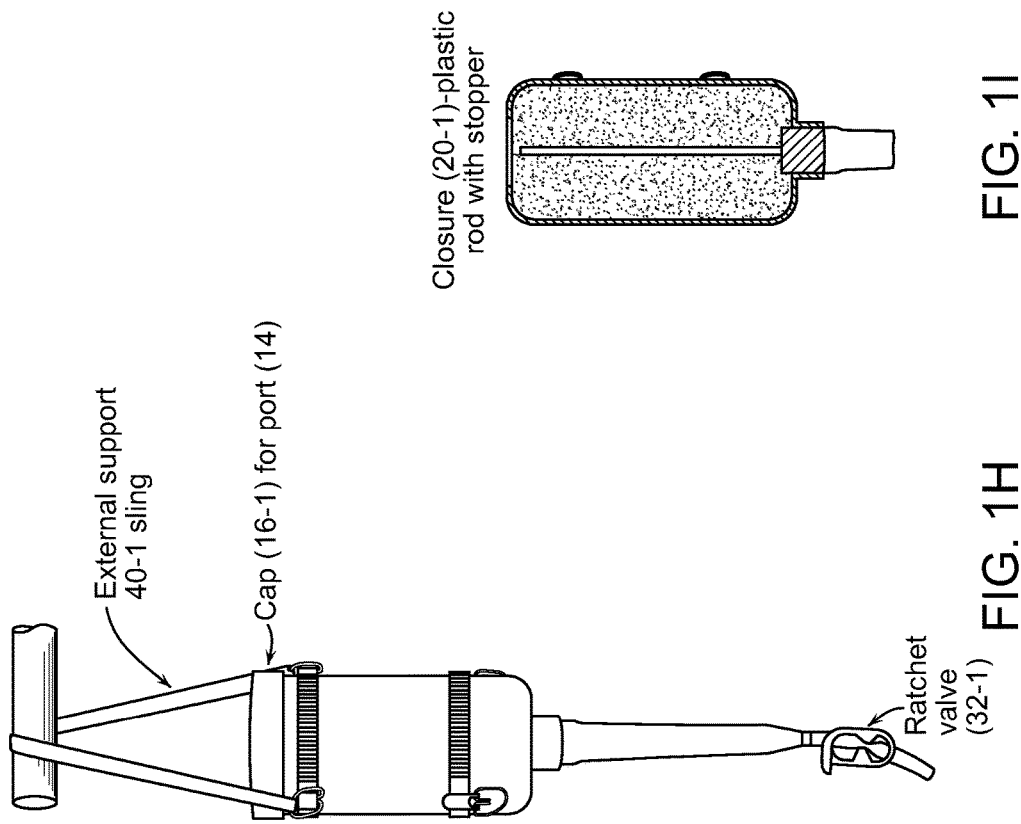
FIG. 1I
FIG. 1H
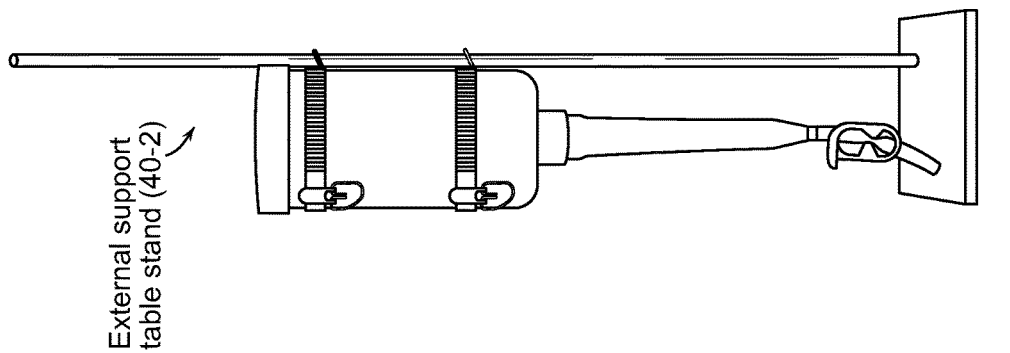
FIG. 1G

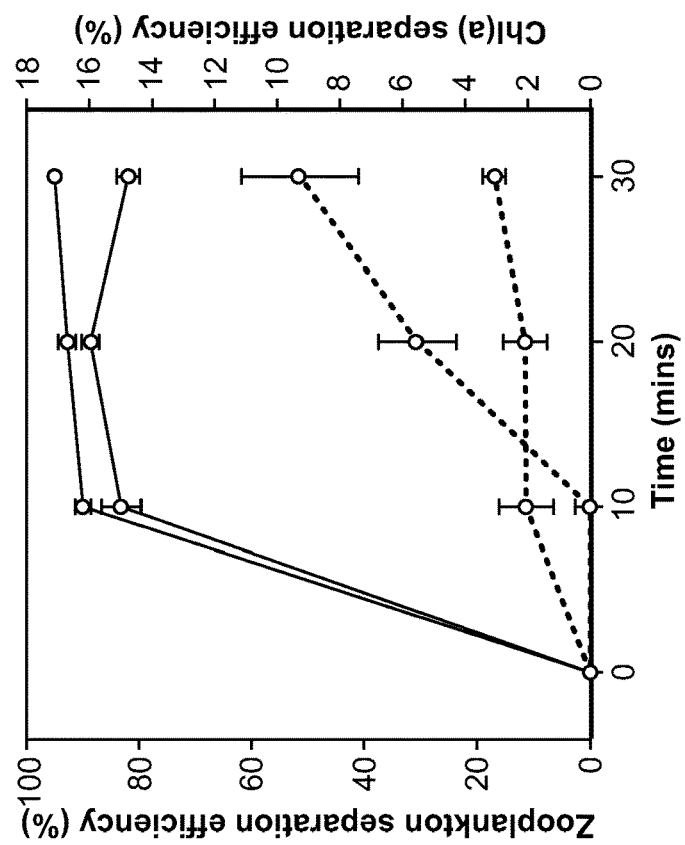
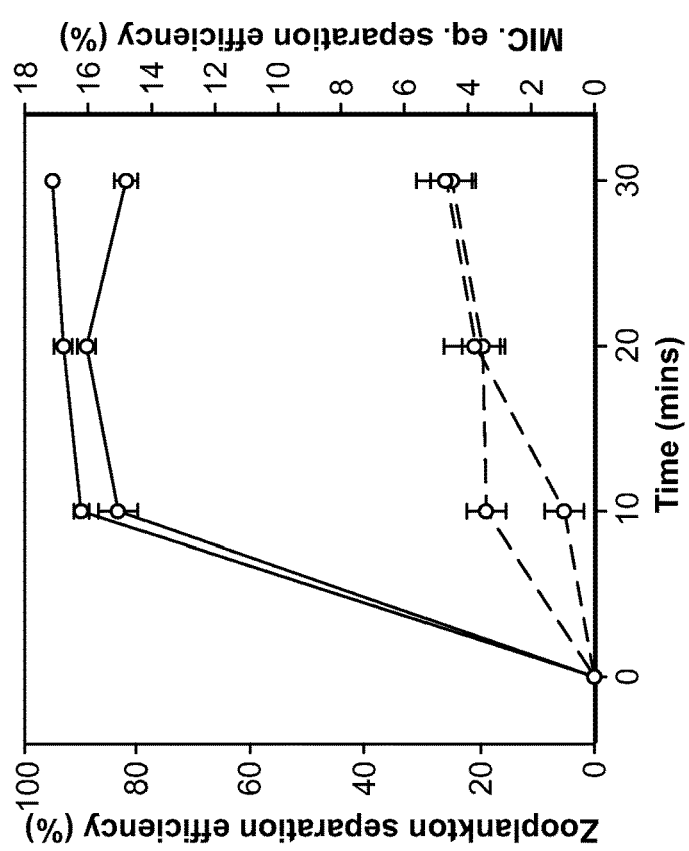
FIG. 7A
FIG. 7B
Separation efficiency curves for macrozooplankton biomass (solid lines) versus microcystic equivalents (dashes) (A) and chlorophyll(a) (B) (dots) in Lake Cochichcwick 4 Sep 2013 and 10 Oct 2013

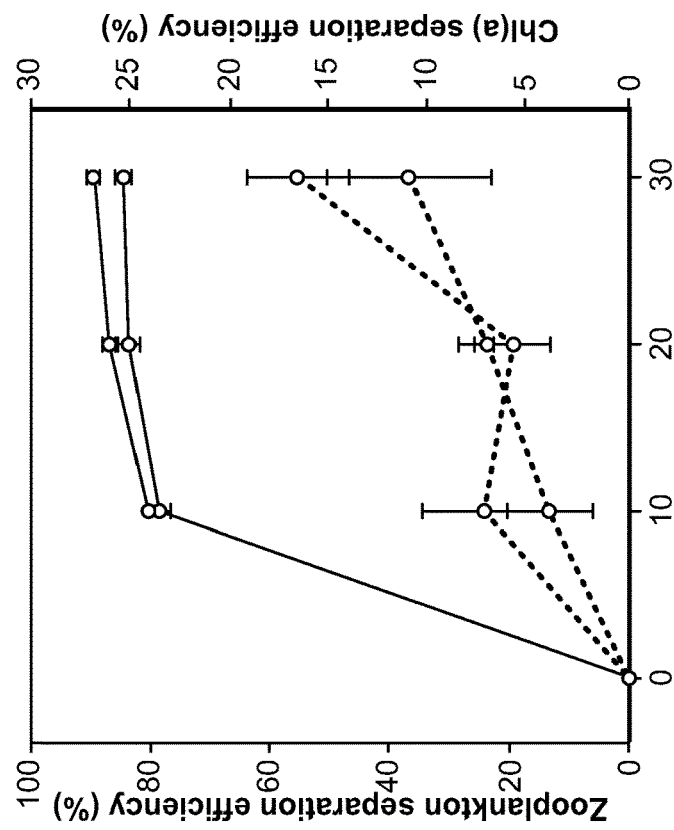
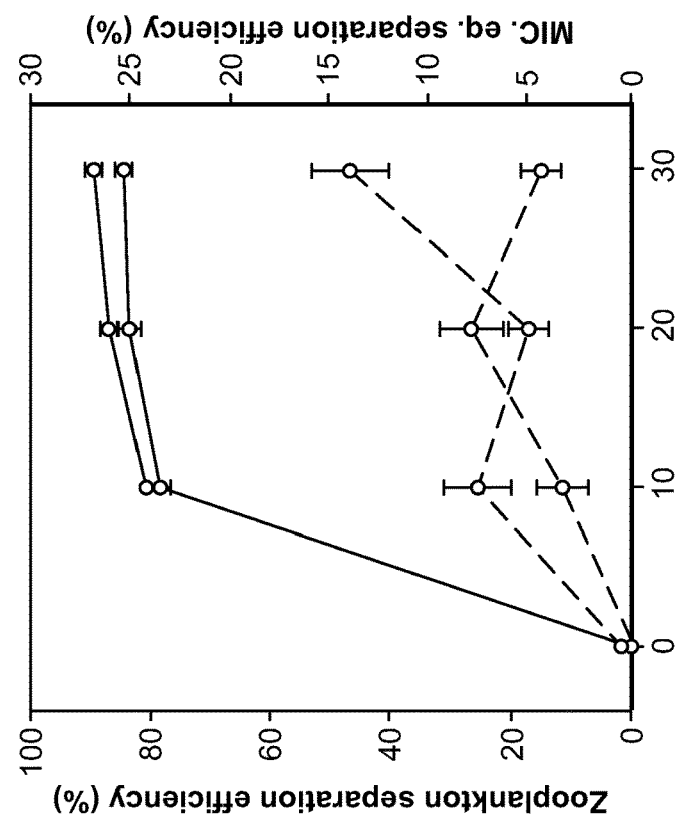
FIG. 7D
FIG. 7C
Separation efficiency curves for macrozooplankton biomass (solid lines) versus microcystic equivalents (dashes) (C) and chlorophyll(a) (dots) (D) in Willand Pond 5 Sep 2013 and 16 Oct 2013.

Separation efficiency curves for macrozooplankton biomass (solid lines) versus microcystic equivalents (dashes) (A) and chlorophyll(a) (B) (dots) in Lake Cochichewick 4 Sep 2013, 10 Oct 2013 (—··—) and 29 Oct 2014 (—···—)

Separation efficiency curves for macrozooplankton biomass (solid lines) versus microcystic equivalents (dashes) (C) and chlorophyll(a) (dots) (D) in Willand Pond 5 Sep 2013, 16 Oct 2013 (— —) and 6 Sep 2014 (– – –)

Effect of minimum diameter on separation efficiency of macrozooplankton in Lake Cochichewick 29 October 2014 with standard errors for each shown. Ambient (t–3.54, df–4, p–.024), Artificial (t–4.90, df–4, p–.008)

Separation efficiencies for individual zooplankters from Lake Cochichewick (29 October 2014) and Willard Pond (6 September 2014).

FIG. 11

Table 1. Separation efficiencies for zooplankton biomass as observed in Lake Cochichewick 2013-2014. Mean values with standard error of the mean.

| | Daphnia mendotae | | | | Daphnia ambigua | | | | Diaphanosoma brachyurum | | | | |
|---|---|---|---|---|---|---|---|---|---|---|---|---|---|
| | 29-Oct-14 | | | | 29-Oct-14 | | | | 4-Sep-13 | | 10-Oct-13 | | 29-Oct-14 |
| | Mean | SEM | | | Mean | SEM | | | Mean | SEM | Mean | SEM | Mean | SEM |
| T=10 | 70.1 | 4.1 | | | 50.3 | 9.0 | | | 81.4 | 2.3 | 66.6 | 7.1 | 40.6 | 9.8 |
| T=20 | 72.2 | 10.7 | | | 59.4 | 7.8 | | | 84.7 | 3.6 | 74.7 | 8.4 | 77 | 11.6 |
| T=30 | 78.2 | 2.4 | | | 61.6 | 2.4 | | | 86.8 | 4.7 | 78.7 | 6.0 | 89.4 | 5.5 |

*Microcyclops rubellus*

| | 4-Sep-13 | | 10-Oct-13 | | 29-Oct-14 | | | Diaptomus spp. | | | | | |
|---|---|---|---|---|---|---|---|---|---|---|---|---|---|
| | Mean | SEM | Mean | SEM | Mean | SEM | | | 4-Sep-13 | | 10-Oct-13 | | 29-Oct-14 |
| | | | | | | | | | Mean | SEM | Mean | SEM | Mean | SEM |
| T=10 | 94.6 | 2.8 | 83.3 | 5.1 | 74.1 | 2.2 | | T=10 | 89.7 | 1.3 | 83.4 | 5.1 | 83.5 | 5.7 |
| T=20 | 100 | 0.0 | 82.5 | 3.5 | 85.6 | 6.6 | | T=20 | 93.4 | 1.1 | 91.3 | 0.8 | 94.7 | 1.1 |
| T=30 | 100 | 0.0 | 87.3 | 4.5 | 88.4 | 3.1 | | T=30 | 95.1 | 0.3 | 80.9 | 3.1 | 95.7 | 1.4 |

Copepodites

| | 4-Sep-13 | | 10-Oct-13 | | 29-Oct-14 | | | Nauplii | | | | | |
|---|---|---|---|---|---|---|---|---|---|---|---|---|---|
| | Mean | SEM | Mean | SEM | Mean | SEM | | | 4-Sep-13 | | 10-Oct-13 | | 29-Oct-14 |
| | | | | | | | | | Mean | SEM | Mean | SEM | Mean | SEM |
| T=10 | 83.7 | 1.4 | 56.9 | 5.1 | 47.6 | 6.2 | | T=10 | 44.9 | 8.4 | 11.3 | 5.8 | 6.26 | 0.8 |
| T=20 | 82 | 3.9 | 50.1 | 1.5 | 69.3 | 2.7 | | T=20 | 47.2 | 5.4 | 29.8 | 9.1 | 9.79 | 0.9 |
| T=30 | 90.2 | 1.5 | 45.2 | 10.1 | 64.9 | 3.6 | | T=30 | 54.2 | 3.1 | 20.7 | 8.3 | 9.35 | 1.1 |

FIG. 12

Table 2. Separation efficiencies for zooplankton biomass as observed in Willand Pond 2013-2014. Mean values with standard error of the mean.

*Daphnia catawba*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 90.1 | 1.3 | 80.7 | 1.5 | 69.9 | 7.0 |
| T=20 | 92.1 | 1.8 | 88.9 | 0.5 | 76.2 | 9.6 |
| T=30 | 94.6 | 1.0 | 90.7 | 2.6 | 83.6 | 6.3 |

*Daphnia ambigua*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 80.9 | 5.8 | 63.8 | 9.0 | 50 | 5.2 |
| T=20 | 89.8 | 2.1 | 77.2 | 11.6 | 59 | 6.1 |
| T=30 | 87.9 | 1.1 | 92.3 | 7.7 | 67 | 2.6 |

*Mesocyclops edax*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 67.3 | 1.7 | 63.9 | 3.5 | 60.5 | 1.9 |
| T=20 | 74.2 | 4.7 | 77.3 | 1.3 | 84 | 4.1 |
| T=30 | 82.5 | 3.1 | 87.9 | 2.4 | 88.1 | 3.5 |

*Diaptomus spp.*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 75.3 | 2.2 | 82 | 2.3 | 61.8 | 8.3 |
| T=20 | 88.5 | 6.7 | 81.2 | 4.2 | 76.6 | 5.4 |
| T=30 | 81.9 | 8.5 | 76.3 | 1.8 | 88.6 | 3.6 |

Copepodites

|  | 5-Sep-13 | | 16-Oct-13 | | 6-Sep-14 | |
|---|---|---|---|---|---|---|
|  | Mean | SEM | Mean | SEM | Mean | SEM |
| T=10 | 40.8 | 4.4 | 38.3 | 2.1 | 28.9 | 3.4 |
| T=20 | 39 | 3.4 | 40.7 | 1.5 | 44 | 4.7 |
| T=30 | 44.7 | 8.7 | 47.5 | 4.7 | 42.4 | 1.4 |

Nauplii

|  | 5-Sep-13 | | 16-Oct-13 | | 6-Sep-14 | |
|---|---|---|---|---|---|---|
|  | Mean | SEM | Mean | SEM | Mean | SEM |
| T=10 | 16.6 | 0.8 | 12.7 | 3.2 | 13.1 | 1.3 |
| T=20 | 18.3 | 1.1 | 10.6 | 0.6 | 13.3 | 2.4 |
| T=30 | 22.7 | 1.7 | 10.2 | 2.7 | 16.9 | 2.2 |

METHOD AND DEVICE FOR PLANKTON SEPARATION

RELATED APPLICATION

This application is a continuation application of U.S. application Ser. No. 14/615,110, filed Feb. 5, 2015, which claims the benefit of U.S. Provisional Application No. 61/936,698, filed on Feb. 6, 2014. The entire teachings of the above-identified applications are incorporated herein by reference.

BACKGROUND OF THE INVENTION

Under certain conditions, algae, bacteria and other organisms create health hazards for humans and animals through the production of toxins or bioactive compounds and/or cause deterioration of water quality from production of high biomass. For example, the presence of toxins in recreational and drinking water can produce many deleterious effects in humans, including but not limited to fever, headache, muscle and joint pain, blisters, stomach cramps, diarrhea, vomiting, mouth ulcers and allergic reactions. In severe cases, seizures, liver failure and respiratory arrest may occur. Therefore, increased occurrence of these organisms and resultant problems is of great concern.

Improving monitoring techniques for surveillance programs and ecological risk assessments would aid in determining how best to manage these aquatic ecosystems, thus, helping to ensure that the waterways are properly managed to maintain their aesthetic, economic, ecological and recreational value.

SUMMARY OF THE INVENTION

The methods and devices of the invention allow the researcher to collect and separate plankton samples for surveillance programs and ecological risk assessments. Fast, easy and cost effective methods and devices are described herein that overcome existing limitations associated with the collection, separation and analysis of samples from waterways. Such limitations can include, for example, spatial and temporal variability, toxigenicity, and varying sample quality.

Methods, devices (e.g., apparatuses) and kits for separating a plankton sample into its component parts utilizing phototactic behavior are described. Specifically, the methods and devices of the claimed invention provide the conditions necessary to initiate, direct and reinforce the movement (e.g., migration) of zooplankton away from phytoplankton in a sample, for use in research requiring separation of plankton samples, for example, to provide measures of phytoplankton and zooplankton biomass. The separated plankton samples can yield measures of biomass in different trophic levels. These samples and measurements can be used for various analyses, including bioaccumulation measurement or evaluation of biological community associations.

In one aspect of the invention, a plankton separating device is described, comprising: a darkened chamber and a collection cartridge (e.g., tube) attached to the chamber for allowing entry of highly directional ambient light, wherein the collection tube is of sufficient length to reinforce migration of the zooplankton, thereby separating the plankton into its component parts.

In one aspect of the invention, a plankton separating device is described, comprising: a darkened chamber having at least one port, wherein the port has a closure; and a collection tube attached to the port of the chamber for allowing entry of highly directional ambient light, wherein the collection tube is of sufficient length to reinforce migration of the zooplankton, thereby separating the plankton into its component parts.

In some embodiments, the closure is a stopper or valve. In particular embodiments, the darkened chamber can be configured to be positioned above the transparent collection tube for operation. The darkened chamber can have an outer perimeter surrounding a central axis. The collection tube can be elongate and extend from the darkened chamber along the central axis, starting beyond a point that makes about a 48° angle to the central axis while extending to the nearest location of maximum outer perimeter dimension of the darkened chamber. This can form a contrast shadow relative to the transparent collection tube, simulating a predator to the zooplankton, minimizing the likelihood that zooplankton that have migrated into the collection tube will migrate back into the darkened chamber. In this way, the zooplankton migration into the tube can be reinforced. Therefore, the collection tube should be of sufficient length to reinforce this negative contrast orientation, and, thus, migration of the zooplankton.

In some embodiments, the collection tube can be transparent and can have one of tapered or straight side walls. The outer perimeter of the darkened chamber and the side walls of the transparent collection tube can be generally round. The transparent collection tube can extend away from the darkened chamber beyond a point that makes about a 20°±2° angle to the central axis while extending to the nearest location of maximum outer perimeter dimension of the darkened chamber. The about 20° angle can continue to form a contrast shadow relative to the transparent collection tube that simulates a predator to plankton. At least about 40% of the length of the transparent collection tube can extend beyond the point that makes the about a 20° angle. The darkened chamber and the transparent collection tube can have outer diameters with a darkened chamber $OD_b$ to transparent collection tube $OD_t$ ratio of about 3-3.5 to 1. The transparent collection tube can have a length with a transparent collection tube length to $OD_t$ ratio of about 3.9-5.2 to 1. These ratios can provide a contrast shadow relative to the transparent collection tube, simulating a predator to zooplankton, and sufficient length in the transparent collection tube for zooplankton to migrate and move away from the darkened chamber to minimize zooplankton collected in the transparent collection tube from migrating back into the darkened chamber.

The device and methods can utilize ambient light and are able to be used in situ. In other words, the devices and methods do not require the use of a light source other than ambient light (e.g., bulb, LED or other illumination). Thus, in some embodiments, the light is ambient. In some embodiments, the device does not include an artificial light source or filter. In some embodiments the device comprises a reflective surface, such as a mirror or foil. In some embodiments, the level of introduced light must be of a sufficient level to initiate positive phototactic movement of the zooplankton to the fluid-filled collection tube. In one aspect, the change in light intensity is sudden. In some embodiments, the stimulus beam of light can be approximately 2 cm, e.g., 21.5 nm or 20 mm.

In some embodiments, the collection tube comprises (e.g., is filled with) a fluid, preferably water, such as filtered water, e.g., in situ filtered water. In some embodiments, the diluent is in situ filtered water to maintain thermal and chemical equilibrium of the environment for the zooplankton.

In some embodiments, the collection tube is transparent, i.e., entirely transparent. In another embodiment, most (for example, approximately at least 85%, e.g., at least 90%, e.g., at least 95%) or all of the tube is transparent, and the remainder of the tube is translucent or opaque. In another embodiment, most (for example, approximately at least 85%, e.g., at least 90%, e.g., at least 95%) or all of the tube is translucent.

In some embodiments, the darkened chamber can have a capacity of at least about one liter, and the collection tube can have a capacity of at least about 50 ml. The opening between the darkened chamber and the transparent collection tube can be, for example, in the range of about 19 mm to 22 mm across. The transparent collection tube can have an inner diameter, with at least a portion of which being about 20 mm to 26 mm. The length of the transparent collection tube can be at least about 110 mm. The ratio of the length of dark region (e.g., darkened chamber) to collection tube length can be about 1-3 to 1.

In one embodiment of the invention, a method for separating plankton is described, comprising acclimating a plankton sample comprising zooplankton and phytoplankton in a darkened chamber for a sufficient amount of time to facilitate a response to a change in light intensity; introducing light at a sufficient level to initiate phototactic movement to a collection tube filled with a fluid (e.g., water, for example, filtered water, such as in situ filtered water), wherein the zooplankton is separated from the phytoplankton; collecting a zooplankton sample from the device; and collecting a phytoplankton sample from the device, wherein the plankton is separated to zooplankton and phytoplankton. In particular embodiments, the plankton sample can be a concentrated sample. The concentrated sample can be diluted.

In another embodiment of the invention, a method for separating plankton is described, comprising acclimating a plankton sample comprising zooplankton and phytoplankton in a darkened chamber for a sufficient amount of time to facilitate a response to a change in light intensity; introducing light at a sufficient level to initiate positive phototactic movement of the zooplankton to a fluid-filled collection tube, said tube being of sufficient length to reinforce negative contrast orientation, wherein zooplankton is separated from phytoplankton, collecting a zooplankton sample from the collection tube; and collecting a phytoplankton sample from the collection tube, wherein the plankton is separated to zooplankton and phytoplankton. In one embodiment of the first aspect, the method further includes analyzing (e.g., studying) the sample. In some embodiments, analysis can comprise, e.g., identification, enumeration, and/or quantification of biomass, quantification of pigment fluorescence, etc.

In some embodiments, the invention relates to a method for separating plankton, comprising placing a plankton sample comprising zooplankton and phytoplankton in a darkened chamber; acclimating the plankton for a sufficient amount of time to facilitate a response by the zooplankton to a change in light intensity; and introducing ambient light to the chamber to initiate phototactic movement of the zooplankton to a collection tube filled with water, the phototactic movement into the collection tube separating the zooplankton from the phytoplankton. In some embodiments, the collection tube is of sufficient length to reinforce contrast orientation. In some embodiments, collection tube is transparent. In some embodiments, the collection tube is located below the darkened chamber at a 90° angle relative to a horizontal base of the darkened chamber. In some embodiments, the collection tube has a length sufficient to ensure that an angle of 48° to normal can be achieved by the zooplankton. In some embodiments, the plankton is acclimated for 20 minutes or less.

In some embodiments, the invention relates to a plankton separation method comprising introducing a plankton sample comprising zooplankton and phytoplankton to a darkened chamber of the devices described herein, acclimating the sample for a sufficient amount of time to facilitate a response to a sudden change in light intensity; introducing highly directional ambient light at a sufficient level to initiate phototactic movement to a collection tube filled with water, said tube of sufficient length to reinforce negative contrast orientation, wherein the zooplankton is separated from the phytoplankton, collecting zooplankton from the collection tube; and collecting phytoplankton from the collection tube, wherein the plankton is separated to zooplankton and phytoplankton samples.

In some embodiments, the invention relates to a plankton separating device comprising a darkened chamber having a port, wherein the port has a closure; and a collection tube attached to the port of the chamber for allowing highly directional ambient light, wherein the collection tube is of sufficient length to reinforce migration of the zooplankton, thereby separating plankton into its component parts, wherein the closure is configured to be changed from a closed state to an open state with the collection tube attached to the port. In some embodiments, the closure is a stopper or valve. In some embodiments, the chamber is configured to be positioned above the collection tube during operation, the chamber having an outer perimeter surrounding a central axis, the collection tube being elongated and extending from the darkened chamber along the central axis, starting beyond a point that makes about a 48° angle to the central axis while extending to the nearest location of maximum outer perimeter dimension of the darkened chamber. In some embodiments, the outer perimeter of the darkened chamber and the side walls of the collection tube are generally round.

In some embodiments of the methods, devices and kits described herein, the collection cartridge (tube) is of sufficient length to reinforce contrast orientation. In some embodiments, collection tube is transparent. In some embodiments, the collection tube is located below the darkened chamber at a 90° angle relative to a horizontal base of the darkened chamber. In some embodiments, the collection tube has a length sufficient to ensure that an angle of 48° to normal can be achieved by the zooplankton. In some embodiments, the collection tube is of a sufficient length to reinforce migration. In some embodiments, the collection tube has one of tapered or straight side walls.

In some embodiments, the collection tube extends away from the darkened chamber beyond a point that makes about a 20°±20° angle to the central axis while extending to the nearest location of maximum outer perimeter dimension of the darkened chamber. In some embodiments, at least about 40% of length of the collection tube extends beyond said point that makes said about a 20° angle. In some embodiments, the darkened chamber and the collection tube have outer diameters with a darkened chamber ODb to transparent collection tube ODt ratio of about 3-3.5 to 1, the transparent collection tube having a length with a transparent collection tube length to ODt ratio of about 3.9-5.2 to 1, thereby providing a contrast shadow relative to the transparent collection tube simulating a predator to plankton, and sufficient length in the transparent collection tube for plankton to migrate from and move away from the darkened chamber to minimize plankton collected in the transparent collection tube from migrating back into the darkened chamber. In some embodiments, the darkened chamber has a capacity of at least about one liter, and the collection tube has a capacity of at least about 50 ml. In some embodiments, the opening between the darkened chamber and the collection tube is in the range of about 19 to about 22 mm across. In some embodiments, the collection tube has an inner diameter, at least a portion of which being about 20 mm to about 26 mm. In some embodiments, the length of the collection tube is at least about 110 mm.

In another aspect, a plankton separation method is described using a device of the invention, the method comprising acclimation of a plankton sample comprising zooplankton and phytoplankton in a darkened chamber of the device for a sufficient amount of time to facilitate a response to a change (e.g., a sudden change) in light intensity; introducing highly directional ambient light for phototactic movement of zooplankton from the darkened chamber to a fluid-filled collection tube of sufficient length to reinforce negative contrast orientation; collecting zooplankton from the collection tube; and collecting phytoplankton from the collection tube, wherein the plankton is separated to zooplankton and phytoplankton.

In another aspect, kits are described. In one embodiment, a kit comprising a plankton separation device of the invention and instructions for using the device is described. In another embodiment, the kit can comprise a darkened chamber and a collection tube. In another embodiment, the kit further comprises filtered water. Educational materials can be included in with kits. Educational materials can include, but are not limited to, any materials which serve to impart knowledge, information, or skills, including, but not limited to, instructions for how to use the device; information regarding how to analyze the samples; information regarding water quality, water studies, and/or plankton; and suggestions for age and/or ability appropriate activities and lab exercises, including for those in age group K-12.

In another aspect, the invention encompasses methods of measurement and assays of plankton and plankton related materials using the methods and devices described herein. For example, in one embodiment, the measurement is a measurement of planktonic biomass.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1G-1I shows further embodiments of the separation device.

FIGS. 7A and 7B are graphs showing separation efficiency curves for macrozooplankton biomass versus microcystis equivalents and chlorophyll in Lake Cochichewick on Sep. 4, 2013 and Oct. 10, 2013.

FIGS. 7C and 7D are graphs showing separation efficiency curves for macrozooplankton biomass versus microcystis equivalents and chlorophyll in Willand Pond Sep. 5, 2013 and Oct. 16, 2013.

FIG. 11 is a table of separation efficiencies for zooplankton biomass as observed in Lake Cochichewick 2013-2014.

FIG. 12 is a table of separation efficiencies for zooplankton biomass as observed in Willand Pond 2013-2014.

DETAILED DESCRIPTION OF THE INVENTION

Figure 1A:
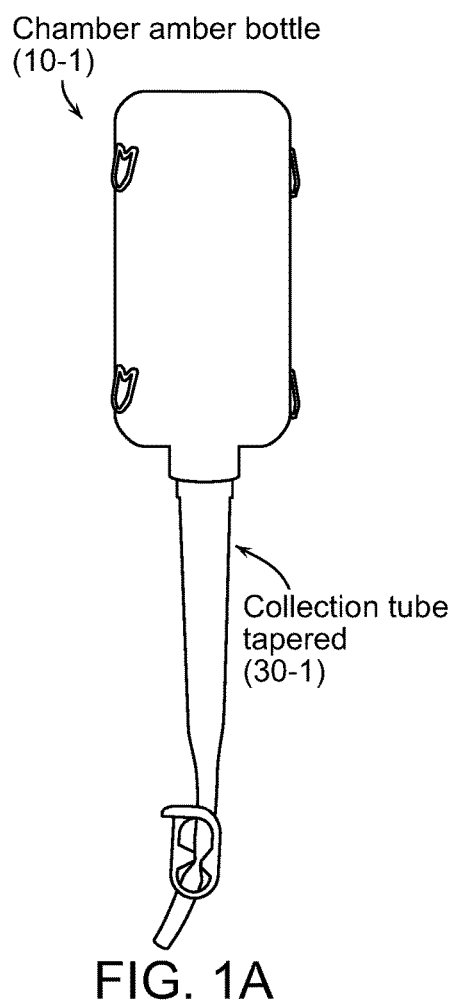
FIGS. 1A-1C show an embodiment of the separation device, having a darkened chamber (10-1; amber bottle), closure for temporary physical separation (20-1, stopper), collection tube (30-1; tube with tapered end) and optional external support (40-1; sling support).
Figure 1B:
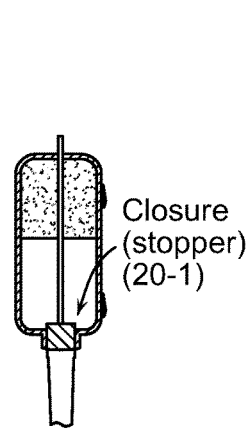
Figure 1C:
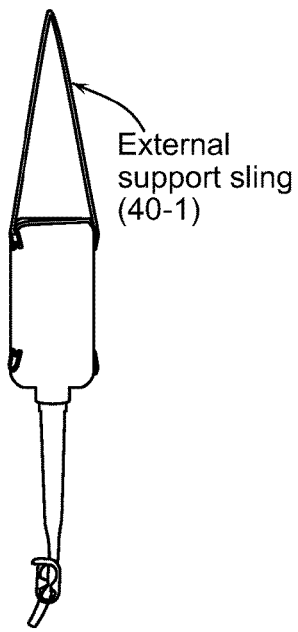

A description of example embodiments of the invention follows.

Described herein are methods and devices for limnological studies using plankton separation, for analysis, bioaccumulation selectivity and evaluation of biological community associations. It was found that the methods and devices of the invention allow the researcher to rapidly collect samples for improved routine surveillance programs and ecological risk assessments in situ.

The structure of planktonic populations in the aquatic ecosystems is dynamic and constantly changing in species composition and biomass distribution. Changes in species composition and biomass distribution may affect separation efficiency.

Plankton, particularly phytoplankton, have long been used as an indicator of water quality. Because of their short life spans, plankton responds quickly to environmental changes. Some species are very sensitive to organic and/or chemical wastes. Some species have also been associated with noxious blooms causing toxic conditions apart from taste and odor problems. The presence of toxins and potential for bioaccumulation threaten fresh water ecosystems, humans and animals.

The physical and chemical characteristics of water affect the abundance, species composition, stability and productivity of indigenous populations of aquatic organisms. The biological methods used for analyzing (e.g., assessing) water quality include, but are not limited to, collection, counting and identification of aquatic organisms; biomass measurements; measurements of metabolic activity rates; toxicity tests; potential for bioaccumulation of pollutants; and processing and interpretation of biological data. The work involving plankton analysis aids in the explanation of the cause of color and turbidity and the presence of objectionable odor, tastes and visible particles in waters; the interpretation of chemical analyse; and the identification of the nature, extent and biological effects of pollution. It also provides data on the status of an aquatic system on a regular basis. The process of plankton separation provides a sample of adequate size and improved quality for postanalytical techniques that include, but are not limited to, assays such as enzyme-linked immunosorbent assay (ELISA), inhibition assays and radioassays.

Numerous studies have been conducted on the occurrence of the cyanobacteria and the toxins that they produce (Carmichael and Falconer 1993, Yoo et al., 1995, Carmichael 1997). Many studies have been conducted to further our understanding of the complex dynamics of cyanobacterial abundance and community composition as they are affected by water temperature, solar irradiance, hydrology, nutrient supply and meteorological conditions. A report (Lopez et al. 2008) outlines current and future efforts that would support and expand understanding of the cyanobacteria, cyanotoxins, ecological impacts, human health effects and management techniques. In the report, the need to improve monitoring techniques was recommended for surveillance programs and ecological risk assessments. For example, routine surveillance programs can be improved with the use of the cost-effective methods and devices described herein to determine the relative contribution of the cyanobacteria to the phytoplankton assemblage. Additionally, the toxigenicity of the cyanobacterial community can be assessed with a rapid, cost effective method to obtain samples that yield precise measures of phytoplankton biomass and weight specific toxicity. This information can be used to determine trends in the ecological integrity of the aquatic systems and support the decision making process regarding use attainment. Ecological risk assessments of bioaccumulation in zooplankton (i.e., bulk zooplankton, macrozooplankton) can be simplified and improved with a rapid, cost effective method to obtain samples that yield precise measures of zooplankton biomass and weight specific toxicity.

Sampling and monitoring of waterways is largely done by state and federal agencies with assistance from volunteers. Methods and devices that are easy to use and do not require expensive or complex systems or parts for obtaining samples are needed. The methods and devices of the present invention meet these needs. Routine surveillance programs are benefited by the cost effective methods and devices described herein that can assess the toxigenicity of the cyanobacterial community. This information can be used to determine trends in ecological integrity and support the decision making process regarding use attainment. The calculation of dry weight biomass and weight specific toxicity is simplified and improved with the methods of the invention for separating plankton samples into its component parts. Routine surveillance programs using biological community associations can be enhanced with a rapid method for collection of samples for analysis. Furthermore, ecological risk assessments are improved using the methods and devices for the evaluation of toxin in different trophic levels, including quantification of cyanotoxins in phytoplankton and the resulting accumulation in zooplankton.

Previous studies have utilized phototactic behavior to separate plankton into its components to quantify cyanotoxins in the phytoplankton and subsequent transfer to the zooplankton (Capron 1995, Johnson 1999, Hathaway 2001, Larsson et al. 2001, Jonasson et al., 2010, Haney 2013, Jonasson, 2013). Phototactic behavior (swimming) is a stimulus response that requires a velocity (kinesis) and a direction (orientation). To take advantage of this naturally occurring phenomenon, the researcher must establish a set of necessary conditions before the phenomenon occurs (Nagel 1974). A hierarchy of response (Loose 1993) to stimulus would include the relative change in light intensity (Ringelberg 1964) which would exceed the rheobase (Ringelberg, 1964, Daan and Ringelberg, 1969) necessary to initiate a swimming response. A positive phototactic response could be anticipated as a result of exposure to a narrow stimulus beam (Forward 1988) (highly directional light) with an angular light distribution that approximates 0° (Schallek 1942). Body axis orientation would result from dorsal beam contrast (45° or less) (Ringelberg 1964) (Ringelberg, Flik and Buis 1975) that would control the direction of movement in the vertical plane. The orientation of the device (darkened above, light below) serves to reinforce body axis orientation as a flight response from predators. The swimming velocity (Daan and Ringelberg, 1969) would have to be sufficient to migrate the distance in the time allowed. Any barriers such as spatial requirements, temperature, pressure, angular light distribution, and other environmental conditions would have to be overcome. In previous studies as noted, the necessary conditions for the phenomenon to occur were met with each researcher modifying the conditions somewhat (spatial requirements, light source, time, distance and temperature). For example, previous researchers provided illumination, followed by waiting 2 hours, five (5) minutes, 15 minutes and twenty (20) minutes before collecting their respective zooplankton samples. In addition, various volumes were collected. These methods resulted in reduced separation efficiency.

The methods and devices of the invention allow for the qualitative and quantitative analysis of plankton. Such studies can monitor the impact of environmental changes on ecological integrity. The methodology and devices simplify and reduce costs associated with monitoring programs while improving the accuracy of the data collected. The device and methods described herein utilize phototactic behavior and contrast orientation for maximal in situ separation of phytoplankton and zooplankton. Further, gathering quantitative data on separation efficiencies, the development of conditions necessary for a desired result based on research objectives can be achieved.

As used herein, "plankton" refers to a diverse group of organisms that live in fresh or salt water. Plankton is usually free floating, suspended in water, nonmotile or insufficiently motile to overcome transport by water currents. Plankton includes phytoplankton and zooplankton.

Phytoplankton generally live near the water surface where there is sufficient light to support photosynthesis. Examples of phytoplankton include, for example, algae, diatoms, cyanobacteria, dinoflagellates and coccolithophores. Phytoplankton can be, for example, unicellular, colonial or filamentous, and is autotrophic (primarily photosynthetic) and can be eaten by zooplankton and other organisms occurring in the same environment.

Cyanobacteria is photosynthetic bacteria found in freshwater and marine environments, including lakes, streams, ponds, the ocean and other surface waters. Cyanobacteria can include planktonic cells or phototrophic biofilms. It can reproduce exponentially to form extensive and highly visible blooms. This blooming cyanobacteria can produce cyanotoxins in such concentrations that they poison and even kill animals and humans. Cyanotoxins can also accumulate in other animals such as fish and shellfish, and cause poisonings such as shellfish poisoning. Among cyanotoxins are some of the most powerful natural poisons known, including poisons which can cause death by respiratory failure. The toxins include neurotoxins, cytotoxins, hepatotoxins, and endotoxins.

Zooplankton include, for example, microscopic protozoans, rotifers, cladocerans and copepods and other aquatic organisms. The species assemblage of zooplankton also may be useful in assessing water quality. Zooplankton can be further separated into size classes, such as macrozooplankton and microzooplankton. Macrozooplankton include, but are not limited to, microcrustaceans larger than 63 ums (microns), including but not limited to Cladocerans: *Bosmina* spp., *Chydorineae* spp., *Ceriodaphnia* spp., *Daphnia* spp., *Diaphanosoma* spp.; and Copepods: Calanoids-female, Calanoids-male (*Diaptomus* spp.), *Microcyclops* spp., *Mesocyclops* spp., and all stages of copepodites. Microzooplankton include, but are not limited to, microcrustacean nauplii and rotifers larger than 20 um, such as 20-63 microns, including, but not limited to: *Keratella* spp., *Kellicottia* spp., *Trichocera* spp., *Asplancha* spp., and *Ascomorpha* spp.

As used herein, "phototaxis" refers to locomotory movement that occurs when a whole organism moves responds to a relative change in light intensity. This can be advantageous for phototrophic organisms as they can orient themselves most efficiently to receive light for photosynthesis. Phototaxis is positive if the movement is in the direction of increasing light intensity and negative if the direction is opposite. The variables that initiate phototactic behavior and maximize migration in the present disclosure include but are not limited to, the relative change in light intensity (e.g., without the use of an artificial light source or filter(s)).

As used herein, "contrast orientation" refers to locomotory movements that occur when a whole organism responds to a spatial change in light intensity. This is advantageous to phototactic organisms as they can orient themselves most efficiently to respond to light/dark boundaries that may indicate the presence or absence of predators. Contrast orientation can be positive or negative.

In some embodiments, the plankton is acclimated in the chamber. Acclimation for a "sufficient amount of time" means a sufficient amount of time to facilitate a response by the plankton to a change in light intensity, for example, between about 20 and about 45 minutes. In one embodiment, the time is about 20 minutes or less, e.g., about 20 minutes.

The selection of plankton separation times can be based on a number of factors, including, for example, the potential for reverse migration by the zooplankton (for example, about 0-60 minutes, e.g., 1 hr.) and phytoplankton contamination of the zooplankton portion as a result of gravity. The desirable phytoplankton "contamination" level typically does not exceed 5%.

As used herein, "sampling" refers to collecting a sample, e.g., a water sample, comprising plankton for monitoring. As used herein, "migration potential" is the distance traveled by an organism in a desired timeframe.

As used herein, "plankton net" refers to a type of field equipment used to trap plankton. It typically has a polyethylene filter of a defined mesh size and a graduated measuring jar attached to the other end. A handle or ring can hold the net. The mesh size of the net determines the size range of the plankton trapped. For example, a mesh of 50 ums can be used for collecting samples.

Example devices are shown in FIGS. 1A-1I. The chamber (10-1) can be of a dark color (e.g., black, amber) and constructed of a durable material, in some embodiments with a conical shape and smooth walled. The chamber is constructed so that light is prevented from entering the chamber during the separation phase. For example, the chamber can have at least one port (12) with a closure for temporary separation (20) (e.g., stopper with plastic rod (20-1), valve, ball valve (20-2) screw cap, or other mechanism to stop fluid communication as needed). In another aspect, the chamber has one or more additional sample port(s) (14) for introduction of the water and/or sample. In certain embodiments, the sample port is located at the top of the chamber and can be of a sufficient size for introduction of sample. The sample port (opening) includes a closure (16), for example a cap (16-1). The port (14) can act as a sample port if there is only one port. The port can have openings to the interior of the chamber that further have a closure.

During the separation phase, the internal chamber is darkened and a temporary physical separation (e.g., a closure) between the chamber and a collection tube (30) is removed. The collection tube is of a sufficient size and material to facilitate migration of the zooplankton. The collection tube is attached to the chamber (10-1) via a port (12) and is transparent or translucent or can become transparent for allowing a sufficient amount of highly directional ambient light to enter and facilitate collection of zooplankton.

In a certain embodiment, the collection tube is conical in shape to facilitate the collection of zooplankton. The length of the collection tube can be selected so that the zooplankton can migrate past a 48° angle to the normal within the tube. The collection tube optionally includes a valve (32) e.g., a ratchet valve (32-1), or clamp to permit or stop flow of the zooplankton. The collection tube can be a tapered tube. In alternative embodiments, the tube has a screw cap on one end and blunt end with cap on the other. The collection tube is of sufficient length for migration and separation of the components of the plankton. In certain embodiments, the separation chamber includes an external support to the device (40) for example, a bridle/sling (40-1) assembly and/or external rings, for positioning the chamber for use with a table stand (40-2) or a clamping device (40-3).

Figures 1D, 1E, 1F:
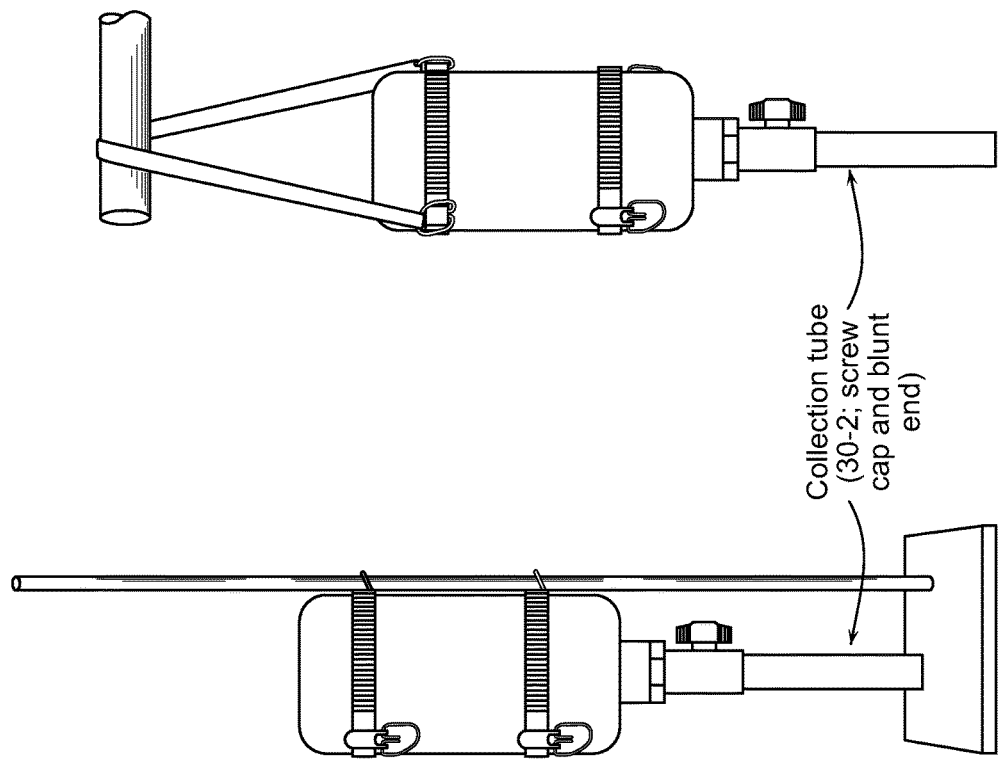
FIGS. 1D-1F show other embodiments of the device, with external support of rings, a table support, and a c-clamp system.
Figure 1J:
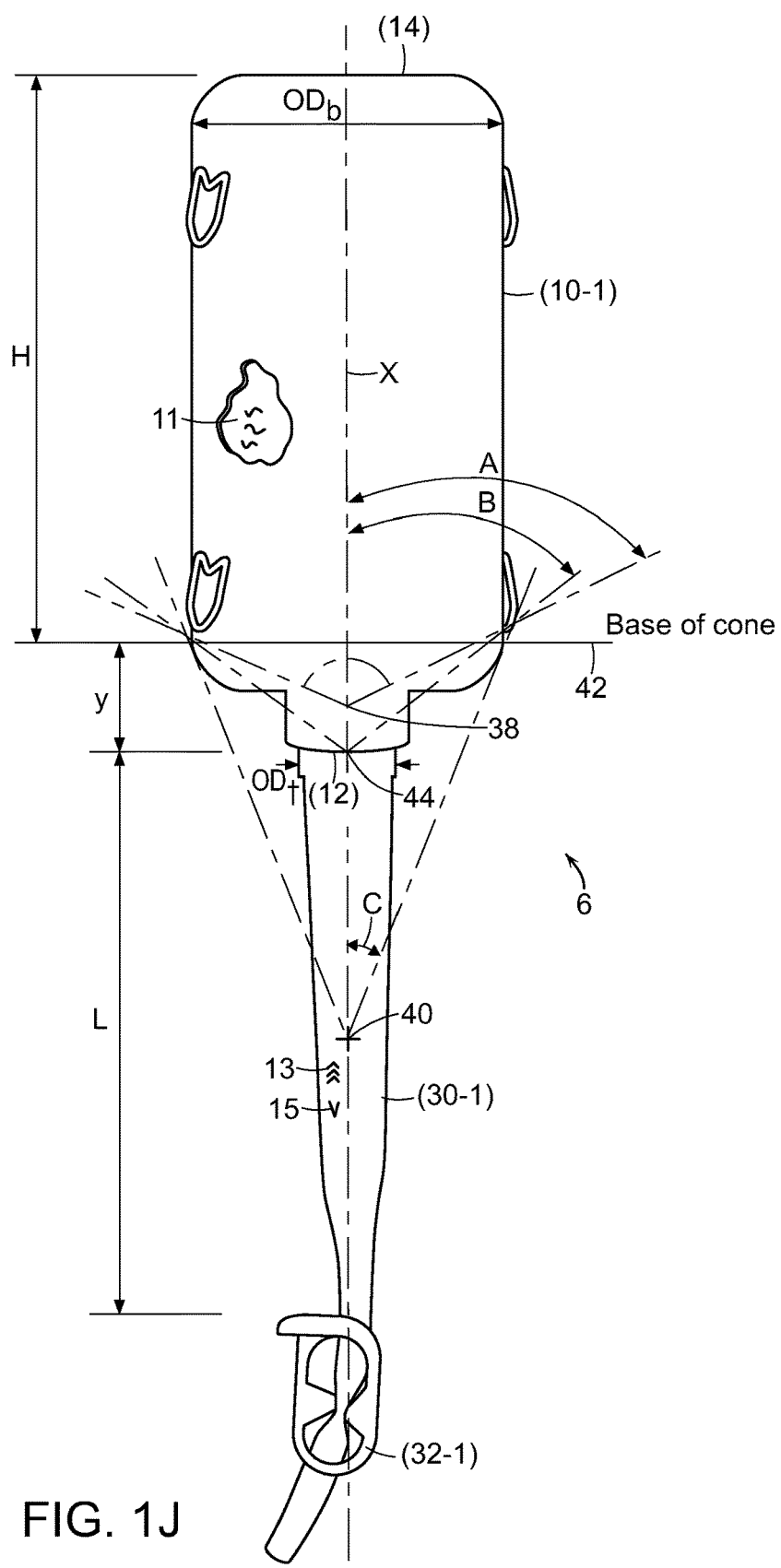
FIG. 1J is a front view of the embodiment of FIG. 1A with annotations.

Referring to FIG. 1J, the darkened container or chamber (10-1) of separating device 6 for containing a sample 11 of water and plankton for separation, can be a generally cylindrical bottle with a circular or round outer perimeter or side wall, and have a height H with a generally constant outer diameter $OD_b$ that concentrically surrounds a longitudinal central axis X. The collection chamber, region, container or tube (30-1) for containing filtered water 13 into which desired plankton 15 can be collected, can be connected to and sealed to the darkened chamber (10-1) at a central outlet, opening or port (12). The collection tube (30-1) can extend in a straight manner from the darkened chamber (10-1) along or aligned with the longitudinal central axis X. The collection tube (30-1) is typically transparent and typically operates with existing ambient light, and can have a tapered shape or side walls, being widest at port (12) and narrowest at ratchet clamp or valve (32-1). In some embodiments, the device comprises a single port.

The separating device 6 can be configured to be used in operation with the darkened chamber (10-1) being positioned above the transparent collection tube (30-1), for example with the longitudinal central axis X being vertical or near vertical. This can allow plankton such as phototactic zooplankton that are attracted to light, such as ambient light on, within or illuminating the transparent collection tube (30-1), to move or swim vertically downwardly from darkened chamber (10-1) with gravity into the transparent collection tube (30-1). Higher percentages of such plankton tend to swim vertically downwardly with gravity to light, in comparison to swimming to light horizontally or laterally, or vertically upwardly against gravity. Therefore, positioning the transparent collection tube (30-1) vertically below the darkened chamber (10-1) can maximize desired plankton migration toward light to obtain maximum or high separation efficiencies. In addition, the port (12) between the darkened chamber (10-1) and the transparent collection tube (30-1) can have a small opening in comparison to the outer perimeter diameter $OD_b$ (about ⅓ in size), which produces a narrow defined circular beam or spot of light with high contrast from the transparent collection tube (30-1) vertically upwardly from below along longitudinal axis X into darkened chamber (10-1), which draws phototactic plankton 15 downwardly vertically into the transparent collection tube (30-1). If the port (12) is too large, too much light can diffuse into the bottom of the darkened chamber (10-1), and not provide enough contrast or definition between dark and light to cause the plankton 15 to migrate into the transparent collection tube (30-1).

The 48° to normal cone angle, is the angle A which is measured 48° relative to the longitudinal central axis X and a line extending from a point 38 along longitudinal axis X that intersects or passes through a horizontal or lateral base line 42 at the widest or maximum perimeter or diameter side wall dimension location of darkened chamber (10-1) that is closest to the transparent collection tube (30-1). The longitudinal axis X is normal to lateral line 42. A shadow of an object such as darkened chamber (10-1) above plankton 15 (such as zooplankton that have migrated into transparent collection tube (30-1)), at a cone angle of 48° or less, can form a concentric contrast shadow relative to the plankton 15 within the interior of the transparent collection tube (30-1). That contrast shadow can simulate a predator to the plankton 15, which tends to cause the plankton 15 to swim downwardly within the transparent collection tube (30-1) away from the darkened chamber (10-1) to maintain separation of the plankton in separating device 6. If angle A is larger than 48°, the shadow of the darkened chamber (10-1) typically does not provide enough contrast between light and dark to the plankton 15 to simulate a predator, and some of the plankton 15 within the transparent collection tube (30-1) tends to migrate back into the darkened chamber (10-1). As can be seen in FIG. 1J, the 48° angle A is located within the darkened chamber (10-1), and the cone angle B measured relative to longitudinal axis X and a line extending from a point 44 along longitudinal axis X, at the transition between the darkened chamber (10-1) and the transparent collection tube (30-1), to the outer perimeter of darkened chamber (10-1) on base line 42, is less than 48°. Angle B is the angle that plankton 15 can migrate past and view the concentric contrast shadow of the darkened chamber (10-1). This angle B is less than 48°, such as 41° in some embodiments, and forms a concentric angle and contrast shadow simulating a predator in all directions when the darkened chamber (10-1) and the transparent collection tube (30-1) are both round, that drives the plankton within the transparent collection tube (30-1) downwardly away from the darkened chamber (10-1). The transparent collection tube (30-1) is sufficiently long enough to allow the plankton 15 to swim far enough downwardly away from the darkened chamber (10-1) with gravity to not migrate upwardly back into the darkened chamber (10-1) against gravity.

In some embodiments, the darkened chamber (10-1) can be a light impermeable plastic, glass or metal bottle for holding a sample 11 of about 1 liter, and the transparent collection tube (30-1) can be a clear or transparent tapered elongate plastic or glass tube for holding or containing about 50 ml of filtered water 13 and collected plankton 15. The darkened chamber (10-1) can have a height H of about 166 mm (6.5 in) with a maximum outer perimeter diameter $OD_b$ portion of about 94 mm (3.7 in) that is constant until reaching the top of the darkened chamber (10-1). The darkened chamber (10-1) can narrow down from the outer perimeter diameter $OD_b$ of 94 mm at line 42 to about 30 mm (1.2 in) at port (12) over a distance Y that can be about 50 mm (2 in). The transparent collection tube (30-1) can have a length L of about 150 mm (5.9 in) between port (12) and ratchet valve (32-1). The transparent collection tube (30-1) can be round and have a maximum outer diameter $OD_t$ at port (12) of about 29.5 mm (1.2 in) with a corresponding inner diameter $1D_t$ of about 21.5 mm (0.85 in). The opening into the transparent collection tube (30-1) from darkened chamber (10-1) can be about 21 mm 2 mm (0.83 in±0.08 in). It has been found that smaller openings into the transparent collection tube (30-1), such as 13 mm, hinder the migration of phototactic plankton and result in lower separation efficiencies. At the ratchet valve (32-1) at the bottom, the outer diameter can taper to about 10 mm (0.4 in) with a corresponding inner diameter of about 7 mm (0.3 in). Port (14) at the top of darkened chamber (10-1) can have a diameter of about 69 mm (2.7 in). Angle B can be about 41°±2°. The transparent collection tube (30-1) can form a narrow circular or round tapering column of water exposed to ambient light, extending downwardly concentrically from darkened chamber (10-1), starting with about ⅓ the diameter of the darkened chamber (10-1).

A cone angle C of about 20°±2°, such as 19°, can extend relative to the longitudinal axis X and a line extending from point 40 along longitudinal axis X within transparent collection tube (30-1) to the maximum outer perimeter diameter $OD_b$ at base line 42. About 40% of the length of transparent collection tube (30-1) can extend downwardly below the 19° angle C. This provides enough downwardly vertical space within transparent collection tube (30-1) where collected plankton 15 can swim downwardly far enough away from darkened chamber (10-1) in response to the simulated predatory contrast shadow produced, where the plankton will not migrate back into the darkened chamber (10-1). The darkened chamber outer diameter $OD_b$ and the transparent collection tube outer diameter $OD_t$ can have an $OD_b$ to $OD_t$ ratio of about 3-3.3 to 1, such as about 3.2 to 1, and there can also be an $OD_b$ to transparent collection tube inner diameter $ID_t$ ratio, $OD_b$ to $ID_t$ ratio of about 4.2-4.6 to 1, such as about 4.4 to 1. The transparent collection tube (30-1) can have a length L to outer diameter $OD_t$ ratio of about 5-5.2 to 1, such as 5.1 to 1, and a L to $ID_t$ ratio of about 6.8-7.2 to 1, such as about 6.9 to 1. The ratio of the dark region length of darkened chamber (10-1) to transparent collection tube length L can be about 1.2-1.6 to 1 such as about 1.4 to 1. Such configurations, dimensions and ratios can maximize separation efficiencies of plankton separation, by using plankton's migration responses to light and predators.

Figure 1K:
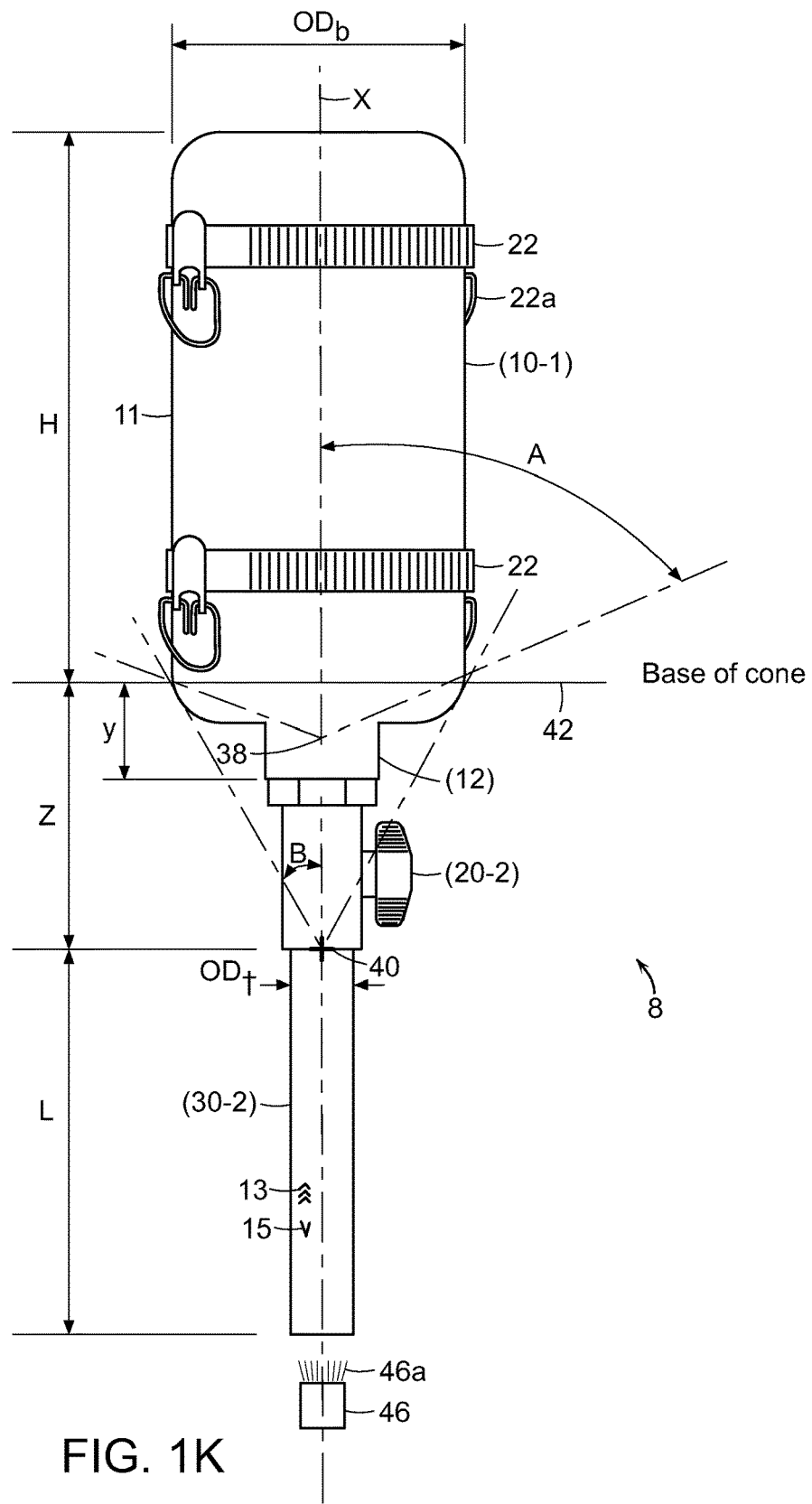
FIG. 1K is a front view of the embodiment of FIG. 1D with annotations.

Referring to FIG. 1K, the darkened chamber (10-1) of separating device 8 can be similar to that in separating device 6, and can have similar construction, shape and dimensions as previously discussed. Separating device 8 can differ in that instead of having a closure stopper (20-1) for initially separating the sample 11 within the darkened chamber (10-1) from the transparent collection tube (30-1), a valve (20-2) such as a ball valve, can be mounted or connected to port (12) of the darkened chamber (10-1), and a transparent collection chamber, region, container or tube (30-2) for typically operating in ambient light, can be connected to the bottom or lower end or outlet of valve (20-2). The location of base line 42 and the 48° cone angle A relative to darkened chamber (10-1) are similar to that in separating device 6. However, the valve (20-2), which can be dark or light impermeable, forms a longer darkened region relative to base line 42 along longitudinal axis X, before reaching transparent collection tube (30-2), that can have a distance Z of about 135 mm (5.3 in). The valve (20-2) can have an opening therethrough with an inner diameter of about 20 mm (0.78 in)±2 mm (0.08 in). The valve (20-2) connected to the darkened chamber (10-1) can form a narrow circular dark column extending concentrically downward from darkened chamber (10-1) before reaching transparent collection tube (30-2), that can be about 121 mm (4.8 in) long. The transparent collection tube (30-2) can extend in a straight manner from valve (20-2) along longitudinal axis X, a length of about 111 mm (4.4 in), and can be round or cylindrical with a side wall having a constant outer diameter $OD_t$ of about 28 mm (1.1 in) and an inner diameter $ID_t$ of about 25 mm (0.98 in). The collection tube (30-2) can form narrow circular, round or cylindrical column of water 13 exposed to ambient light, extending downwardly concentrically from darkened chamber (10-1) and valve (20-2), having about ⅓ the diameter of darkened chamber (10-1).

The transparent collection tube (30-2) can be used for containing about 50 ml of filtered water 13 and collected plankton 15. The use of the ball valve (20-2) instead of closure stopper (20-1) can provide separating device 8 with more consistent separation results than with separating device 6. The ball valve (20-2) can open the path or port (12) between the darkened chamber (10-1) and the transparent collection tube (30-2) in a repetitive smooth consistent manner, with a twist of a knob. With regard to closure stopper (20-1) in separating device 6, a stopper is pushed into or pulled from port (12) by a stick or rod. Cone angle B is measured relative to longitudinal axis X and a line extending from a point 40 along longitudinal axis X at the transition between the darkened valve (20-2) and the transparent collection tube (30-2), that intersects the outer diameter $OD_b$ at base line 42, and is less than 48°. In some embodiments, angle B can be about 20°±2°, such as 19° and can form a concentric contrast shadow of the darkened chamber (10-1) relative to the plankton 15 within the interior of the transparent collection tube (30-2) that effectively simulates a predator to the plankton 15. This can cause the plankton 15 to swim downwardly with gravity within transparent collection tube (30-2) away from the darkened chamber (10-1) to maintain separation of desired plankton. Although a 19° angle B is less than half that of 48°, the 19° angle is very effective to prevent plankton 15 within transparent collection tube (30-1) from migrating back into darkened chamber (10-1) against gravity, and the full length L of transparent collection tube (30-2) extends below point 40 of the 19° angle B to allow plenty of room for the plankton 15 to migrate downwardly away from darkened chamber (10-1) and valve (20-2) with gravity. The darkened chamber outer diameter $OD_b$ and the transparent collection tube outer diameter $OD_t$ can have an $OD_b$ to $OD_t$ ratio of about 3.3-3.5 to 1, such as 3.4 to 1, and there can also be an $OD_b$ to transparent collection tube inner diameter $ID_t$ ratio, $OD_b$ to $ID_t$ ratio of about 3.5-4 to 1, such as 3.8 to 1. The transparent collection tube (30-2) can have a length L to outer diameter $OD_t$ ratio of about 3.9-4.2 to 1, such as 4 to 1, and a L to $ID_t$ ratio of about 4.2 to 4.6 to 1, such as 4.4 to 1. The ratio of the dark region length consisting of darkened chamber (10-1) and valve (20-2) to transparent collection tube length L can be about 2.5-2.9 to 1, such as 2.7 to 1. About 40% of the darkened region can be a narrow or circular column extending through valve (20-2). These configurations, dimensions and ratios can also maximize separation efficiencies of plankton separation, and also uses plankton's migration responses to light and predators. Although separating devices 6 and 8 typically make use of ambient light entering transparent collection tubes (30-1) and (30-2). If desired, a reflector or a light source 46 can be used and positioned below or to the side of the devices 6 and 8 for directing light 46a upwardly into collection tubes (30-1) and (30-2).

The separation devices 6 and 8 are able to obtain higher separation efficiencies of plankton than prior devices. The stopper (20-1) or valve (20-2) can keep the sample 11 to be separated, both physically and phototactically isolated within the darkened chamber (10-1) from the transparent collection tubes (30-1) and (30-2), until opened. The vertical orientation of the darkened chamber (10-1) being above the transparent collection tubes (30-1) and (30-2) with a circular beam or spot of light being directed vertically upward through a relatively small port (12) in the darkened chamber (10-1) provides defined light to dark contrast that promotes initial migration of phototactic plankton 15 downwardly toward the light while assisted by and in the direction of gravity. The opening between the darkened chamber (10-1) and the transparent collection tube is sized small enough to provide an attractive defined high contrast beam of light, while large enough not to impede plankton migration. An opening that is too large can let too much light into the darkened chamber (10-1) so there is not a sufficient light to dark contrast, and not promote migration. The transparent collection tubes extend straight down from the darkened chamber (10-1) so that migrating plankton 15 can swim past a 48° angle or less to the longitudinal axis X as described above, such as beyond a 41° point or a 19° or 20° point, within the transparent collection tube. The plankton 15 view the concentric contrast shadow of the darkened chamber (10-1) as a predator and tend to move downwardly with gravity, and not migrate back into the darkened chamber (10-1) against gravity. By having a large enough collection sample, such as at least 50 mls, the transparent collection tube can have a length that is long enough for the plankton 15 to swim far enough downwardly away from the darkened chamber (10-1) and not to migrate back in. The transparent collection tube can extend at least about 40% of the length L of the transparent collection tube beyond the point that makes about a 20°±2° angle to the longitudinal axis X as previously described. In separating device 8, the whole length L of transparent collection tube (30-2) extends beyond the point of the 19° or 20° angle. By having a relatively narrow diameter transparent collection tube, the contrast shadow that the plankton 15 therein sees, can have a relatively consistent viewing angle in all directions. Although particular dimensions have been given, the dimensions can vary, for example, larger darkened chambers and transparent collection tubes can be used.

Figures 1L, 1M:
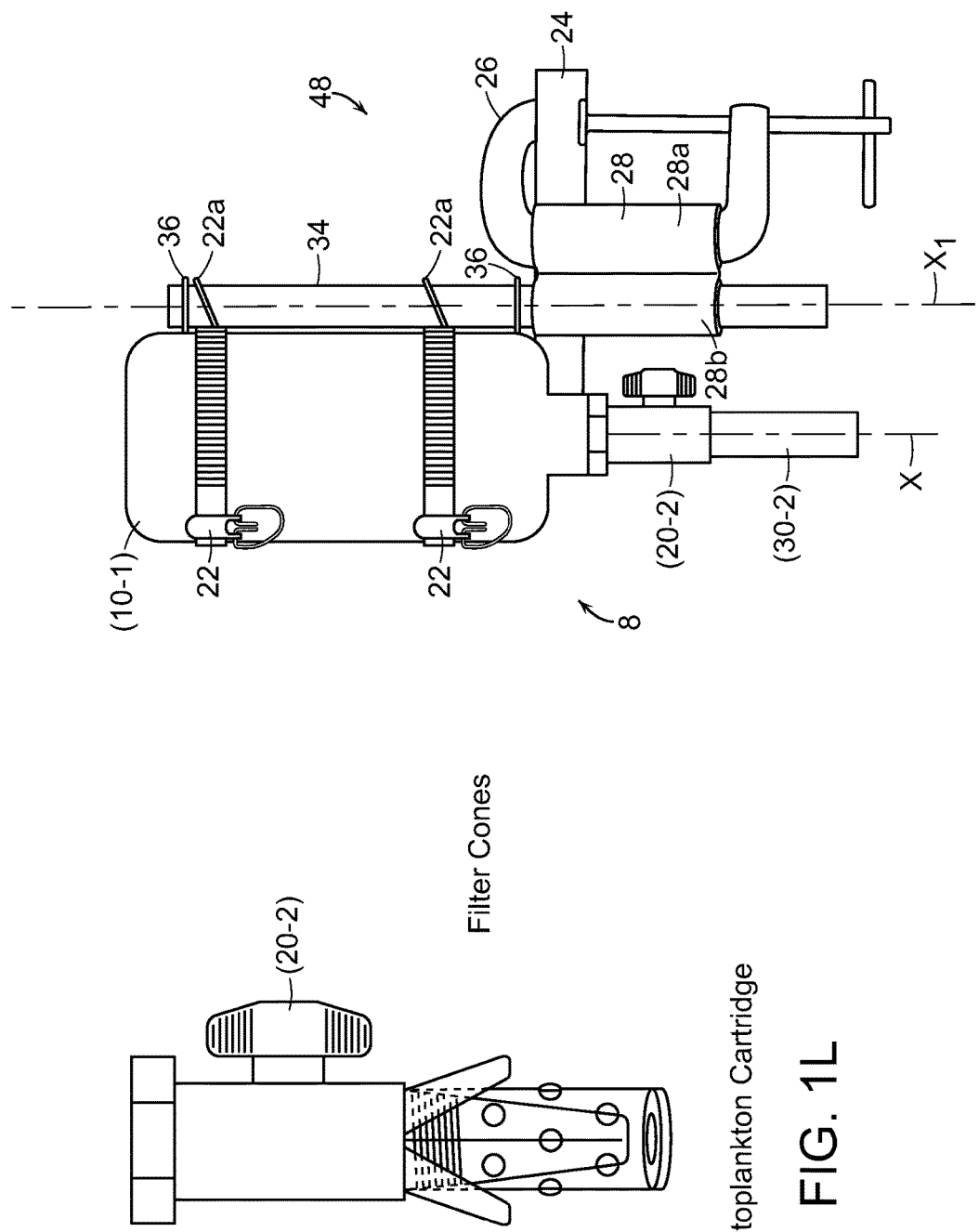
FIG. 1L is a front view of a ball valve connected to a filter cone and cartridge.
FIG. 1M is a side view of an embodiment of a separation device in the present invention including a securement arrangement.

Referring to FIG. 1L, valve (20-2) can be connected to a phytoplankton cartridge and filter cones for processing, as desired.

Figure 1N:
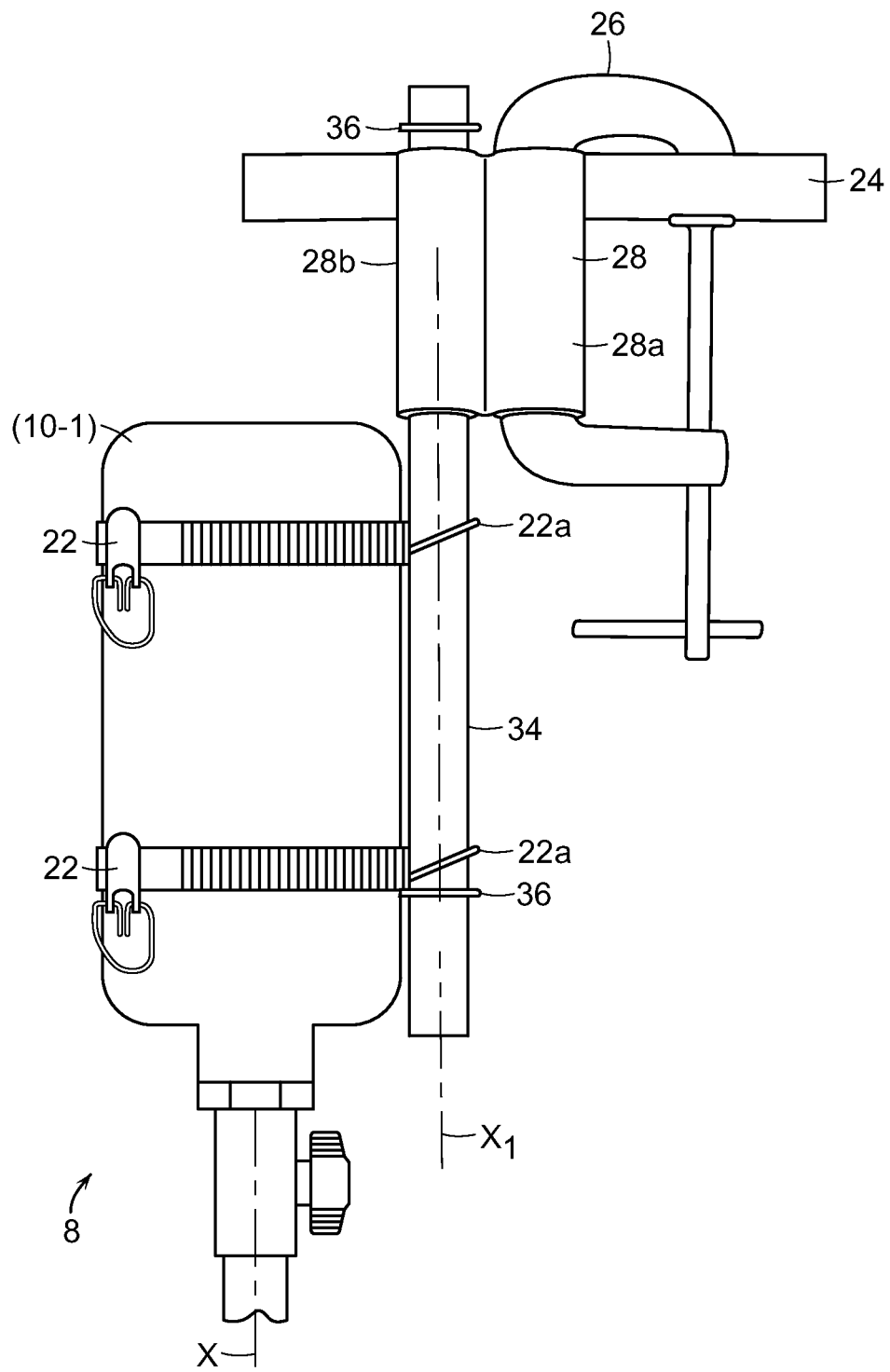
FIG. 1N is a side view showing another configuration of the securement arrangement of FIG. 1M.

Referring to FIG. 1M, separating device 8 can be mounted by a mounting device bracket or arrangement 48, for example, to a surface or rail, such as on a boat or canoe for use or testing on the water. The mounting device 48 can have a C-clamp 26 for securement to the desired surface or rail 24. A bracket body 28 can have a portion 28a secured to or around a vertical member of the C-clamp 26, and a portion 28b for rotatably or pivotably mounting a pivot rod 34 therein about a vertical axis $X_1$. The separating device 8 can have two spaced securement bands 22 around the darkened chamber (10-1) with securement fixtures 22a that secure the separating device 8 to the pivot rod 34. The pivot rod 34 can have stop members 36. The pivot rod 34 can allow the separating device 8 to be pivotably adjusted about axis $X_1$. The separating device 8 can be positioned to extend above C-clamp 26 as shown in FIG. 1M, or below as seen in FIG. 1N.

The devices, methods and kits can be used together or separately to obtain of well-separated samples of phytoplankton and/or zooplankton. One of skill in the art will recognize that modifications and adjustments to the device, kits and methods are encompassed by the scope of the invention described herein.

While this invention has been particularly shown and described with references to example embodiments thereof, it will be understood by those skilled in the art that various changes in form and details may be made therein without departing from the scope of the invention encompassed by the appended claims.

EXAMPLES

Devices were developed that provides the conditions necessary to initiate and direct the movement of zooplankton. Experiments were conducted in Lake Cochichewick and Willand Pond to evaluate separation efficiency for zooplankton and phytoplankton as measures by zooplankton biomass, microcystis equivalents and chlorophyll (a). The evaluation included an original design (2013) and an improved design (2014). There was no significant difference in zooplankton separation efficiencies for either lake between sampling years. Significant reduction in amount and variability of microcystis equivalents and chlorophyll(a) was observed in 2014. The methods and devices allow for the rapid collection of samples for surveillance programs and ecological risk assessments. This is part of an ongoing study to evaluate the device and method in different conditions and over seasonal cycles, and in other environments where questions regarding the presence of toxic substances and their potential for bioaccumulation exist.

Example 1

Materials and Procedures
Collection and Processing of Plankton Samples
The study sites included Lake Cochichewick in North Andover, Mass. (August-October 2013) and Willand Pond in Dover, N.H. (September-October, 2013). Lake Cochichewick is classified as a mesotrophic system and Willand Pond is classified as an oligotrophic system. Concentrated plankton samples for testing were collected from the deep sites between the hours of 10 AM-2 PM using a vertical tow by lowering a 50 nm nylon mesh 30 cm open ring conical plankton net fitted with a 50 um mesh bucket to a depth of 5 m (volume filtered=350 L) and raising vertically at a speed approximating 0.5 m/s. The total number of plankton samples collected depended upon the number of trials to be conducted that day. For example, if twelve (12) trials are conducted, twelve (12) samples are collected. The concentrated plankton samples were placed together in one (1) L. darkened HDPE bottles. Typically, eight (8) to ten (10) concentrated samples are collected in a single bottle, and two bottles of concentrate collected for testing.

Whole lake water was collected in 1 liter darkened HDPE bottles as a surface grab sample to be used as diluent for the concentrate, and as supply for filtered lake water. The concentrated samples were combined in a 5 liter container, mixed, and split using a Folsom plankton splitter until 100 ml aliquots were obtained. The whole lake water (diluent) was combined in a series of 5 liter containers and split using a Folsom plankton splitter until 850 ml aliquots were obtained. The individual concentrate portions (100 mls) were combined with the individual diluent portions (850 mls) for a total of 950 mls of plankton sample, and placed into darkened HDPE bottles. Typically 24 bottles of plankton were prepared in this manner. Filtered lake water was prepared by filtering 1 liter of whole lake water through a 50 um mesh ring net and placing it in a 1 liter beaker. Prior to use in the separation device, filtered lake water samples were analyzed following quantification.

Plankton Separation Efficiency:
Step 1. A separation device was suspended using a sling apparatus. The collection tube was closed off using the ratchet clamp, and filled with filtered lake water. The collection tube was then physically separated from the chamber with the use of a black rubber stopper attached to a plastic rod. The plankton sample was then poured into the chamber. When volume series, time series or calibration series were conducted, as many separation devices as needed were prepared in this manner concurrently. For example, when a time series for 0, 10, 20 and 30 minutes was conducted, four (4) separation devices were prepared. The rubber stopper was removed, the lid placed on top of the chamber and the timer set for the desired time interval.

Collection of Zooplankton and Phytoplankton
Step 2. At the desired time interval, the desired volume of sample was released from the collection tube by opening the ratchet clamp, dispensing the sample into an appropriate container, and then closing the ratchet clamp. This sample was marked as the "Z" (zooplankton) portion. The remainder of the sample was released from the collection tube by opening the ratchet clamp and dispensing the sample into a 1 L. carboy. This sample was marked as the "P" (phytoplankton) portion.

Quantification

Step 3. Phycocyanin (PC) and Chlorophyll (a) (Chla) for the "Z" portion and "P" portion were quantified in vivo, using intact cells without filtration or extraction, using a two-channel hand held AquaFluor fluorometer (Turner Designs, Sunnyvale, Calif.). Using a disposable pipette, 5 mls of each "Z" portion and each "P" portion was placed into a Turner Design methacrylate cuvette. Large specimens of zooplankton were removed from the cuvette using a small tipped disposable pipette prior to analysis. The filled cuvette was placed in the fluorometer and, using channel A, the relative fluorescence units for PC were recorded. Without removing the cuvette from the instrument, channel B was selected and relative fluorescence units for Chla were recorded. PC (excitation at 595 run, emission at 670 nm) was standardized (R2=0.99, p<0.0000, Microcystis equivalents (MIC eq.)=1369 (x)+4245) using *M. aeruginosa* 2385. Chlorophyll a (excitation at 460 nm, emission >665 nm) was standardized (R2=0.99, p<0.000, Chla=8624 (x)−120812) with solid secondary standard (No. 8000-952, Turner Designs). The PC and Chla value of the "Z" portion was adjusted (Adj. Z) to account for the background in the filtered water. The MIC (eq). and Chl(a) concentration/ml were adjusted to reflect volumes collected. The proportion of MIC (eq.) or Chl(a) (separation efficiency) in the "Z" portion for each sample was calculated as follows:

(Adj. Mic. eq. "Z")/(Adj. Mic. eq. "Z")+(Mic. eq. "P")=Separation efficiency for cyanobacteria   Eq. 1

(Adj. Chl(*a*) "Z")/(Adj. Chl(*a*) "Z")+(Chl(*a*) "P")=Separation efficiency for phytoplankton   Eq. 2

Step 4. The "Z" portion was preserved using 5% formalin/sucrose. See Haney, J. F. & D. J. Hall, 1973, "Sugar coated *Daphnia*: A preservation technique for Cladocera," *Limnol. Oceanogr.* 16: 970-977. The "P" portion was filtered through a 50 um mesh ring net, backwashed and brought to an appropriate volume using filtered lake water, and preserved using 5% formalin/sucrose.

Identification and Counting

Step 5. Zooplankton in each "Z" and "P" sample were identified, enumerated and measured. A minimum of 200 individuals were counted in a known subsample volume. The body length (and width as needed) of the first 20 individuals encountered for each genus and/or species was measured. If needed, the count data of the "P" portion was adjusted (Adj. P) to reflect the proportions of sample removed above to quantify phycocyanin and Chlorophyll (a). The count data for the "Z" and "P" portion were adjusted to reflect total sample volume. Dry weight estimates for *Daphnia* spp. *Diaphanosoma* spp., Copepods and *Bosmina* spp. were calculated according to Bottrell, H. H., A. Duncan, Z. M. Gliwicz, E. Grygierek, A. Herzig, A Hillbricht-Ilkowska, H. Kurosawa, P. Larsson, and T. Weglenska, 1976, "A review of some problems in zooplankton production studies," *Norw. J. Zool.*, 24:419-456, *Chydorus* spp. was calculated according to Dumont, H. J., I. van de Velde, and Dumont, S., 1975, "The dry weight estimate of biomass in a selection of Cladocera, Copepoda and Rotifera from the plankton, periphyton and benthos of continental waters," *Oecologia*, 19:75-97. Rotifers were calculated according to EPA Great Lakes National Program Office, 2003, "Standard operating procedure for zooplankton analysis," *LG*403, Revision 3 Feb. 2003, and nauplii were assigned a constant dry weight of 0.40 ug. The proportion of zooplankton biomass (separation efficiency) in the "Z" portion for each sample was calculated as follows:

(Dry wt. "Z")/(Dry wt. "Z")+(Dry wt. (Adj.) "*P*")=Biomass separation efficiency for zooplankton   Eq. 3

The proportionate values were arcsine transformed (Zar, Jerrold H., *Biostatistical Analysis*, Prentice-Hall, Inc. New Jersey, 1974 ed.) and appropriate statistical analysis performed.

Assessment:

The desired volume of the darkened chamber was one (1) liter. The physical requirements of the collection tube (transparent, preferably conical and allowing migrating animals to exceed 48° to the normal) suggested a long, narrow tube or tubing. A tube which measured 1" (D)×8" (L), had a maximum volume of 75 mls, and exceeded the 48° angular criteria at a volume of approximately 50 mls was used. In this embodiment, a stopper was used to provide a temporary physical separation between the chamber and the collection tube. The separation time and volume of the zooplankton and/or phytoplankton samples to be collected were undetermined. Experiments were designed to evaluate the device performance for separation of zooplankton with samples from Lake Cochichewick (August 1) using the methods described in Steps 1-2 and Steps 4-5.

First Experiment

The first experiment (August 1) was designed to evaluate separation efficiencies for zooplankton using the methods described in Steps 1-2 and 4-5.

Figure 2:
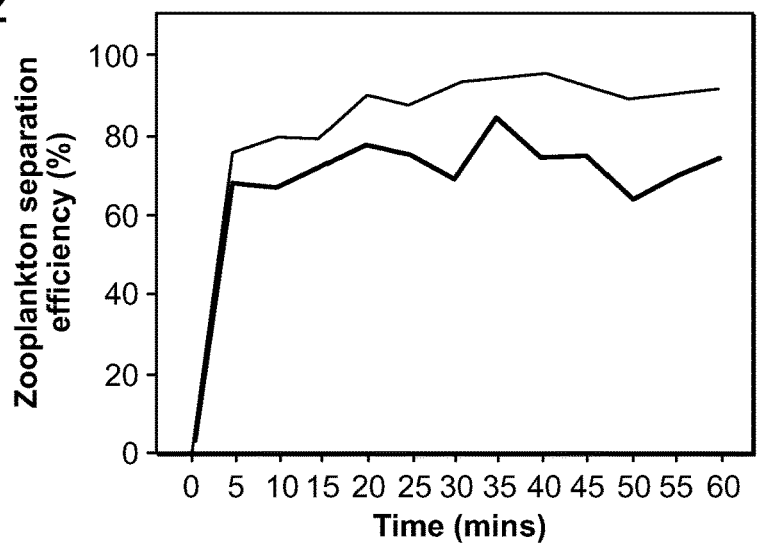
FIG. 2 is a plot showing the separation efficiency for macrozooplankton (top line) and microzooplankton (bottom line) on Aug. 1, 2013 (Experiment 1) "Z"=zooplankton, 50 mls., "P"=phytoplankton, 900 mls.

The results in FIG. 2 indicate that the greatest separation efficiency occurred at T=40 minutes for macrozooplankton and microzooplankton. Separation efficiencies greater than 90% occurred at T=20 minutes for macrozooplankton.

Second Experiment

Figure 3A:
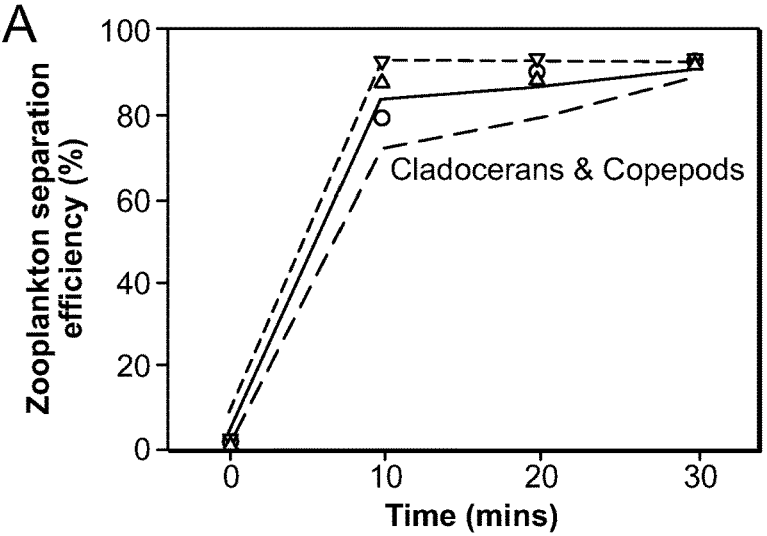
FIG. 3A and FIG. 3B are plots showing mean separation efficiencies for macrozooplankton and microzooplankton in Lake Cochichewick (A) and Willand Pond (B) on Sep. 4 and Sep. 5, 2013, respectively.
Figure 3B:
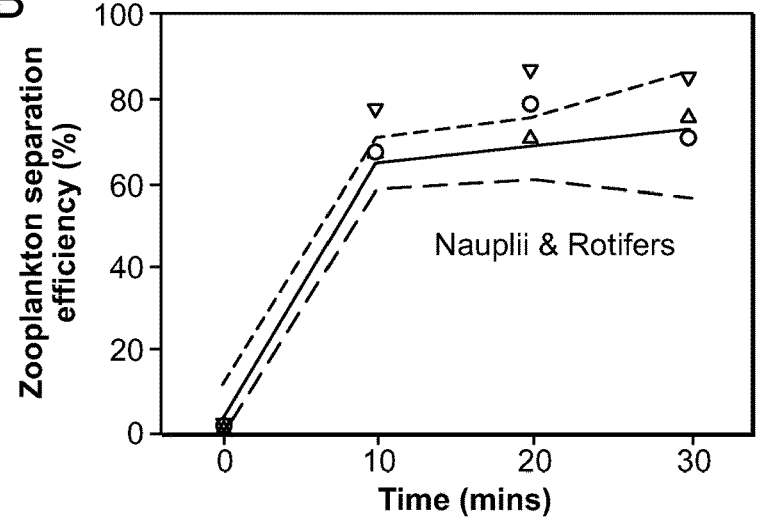

The experimental design was modified to evaluate separation efficiencies using the methods described in Steps 1-5. Additional experiments were conducted using samples from Lake Cochichewick (September 4) and Willand Pond (September 5) with the results shown in FIG. 3A and FIG. 3B. The macrozooplankton consistently had the highest mean separation efficiency for both lakes. The macrozooplankton comprised 89% of the biomass in Lake Cochichewick and 71% of the biomass in Willand Pond.

Figure 4A:
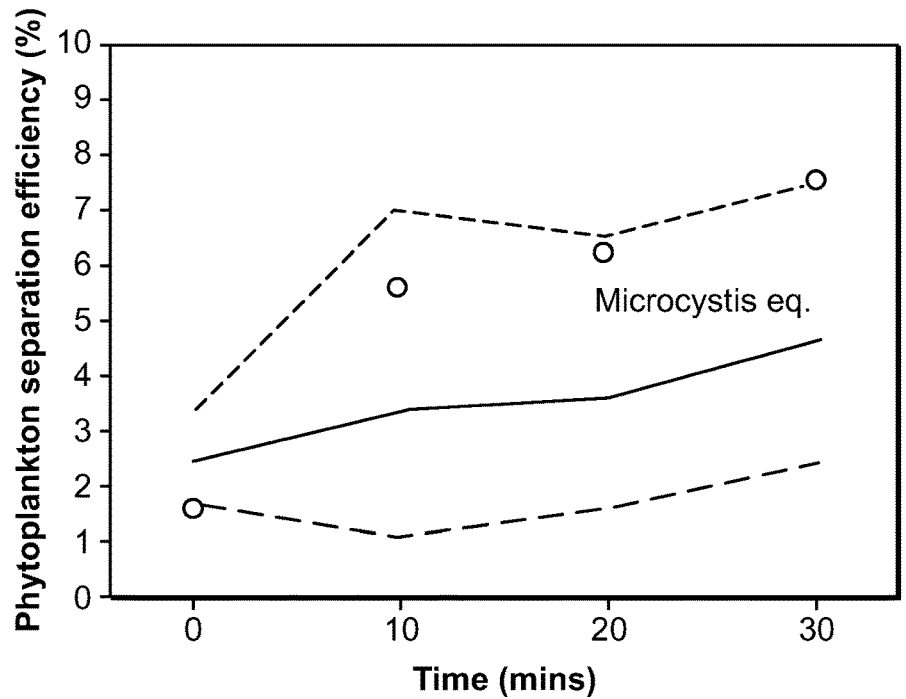
FIG. 4A and FIG. 4B are plots showing calibration curves for macrozooplankton (solid line), cyanobacteria (dashed line), and all phytoplankton (dotted line) for Lake Cochichewick (A) and Willand Pond (B) on Sep. 4 and Sep. 5, 2013, respectively. Confidence intervals (95%) shown as gray lines. Df=4. "Z"=zooplankton, 50 mls, "P"=phytoplankton, 900 mls.
Figure 4B:
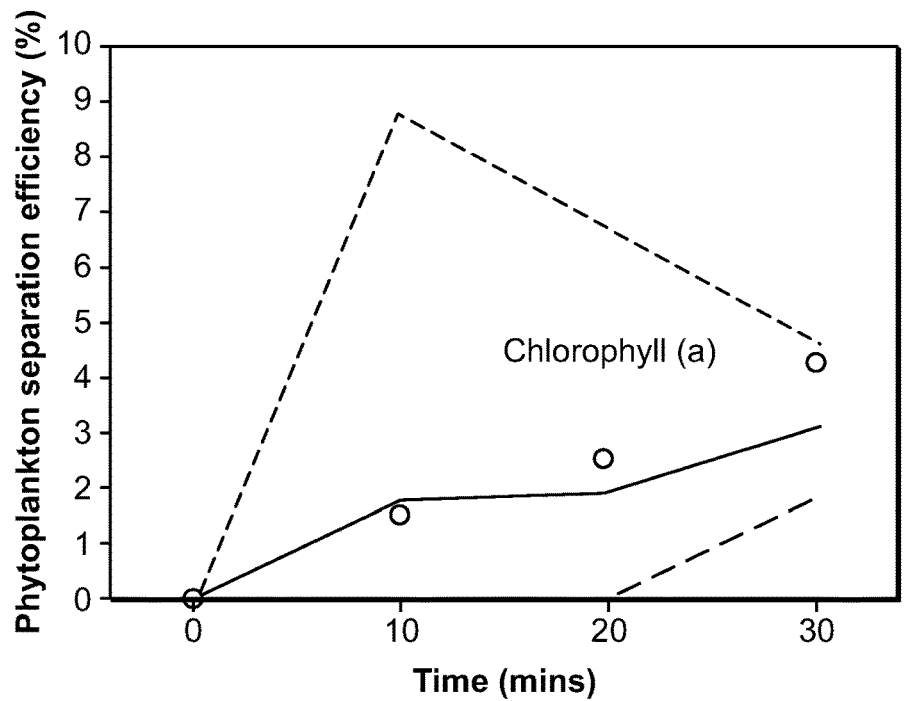

FIG. 4A and FIG. 4B are plots showing calibration curve for macrozooplankton (solid line), cyanobacteria (dashed line), and all phytoplankton (dotted line) for Lake Cochichewick (A) and Willand Pond (B) on Sep. 4 and Sep. 5, 2013, respectively. Confidence intervals are shown in gray.

Figure 5A:
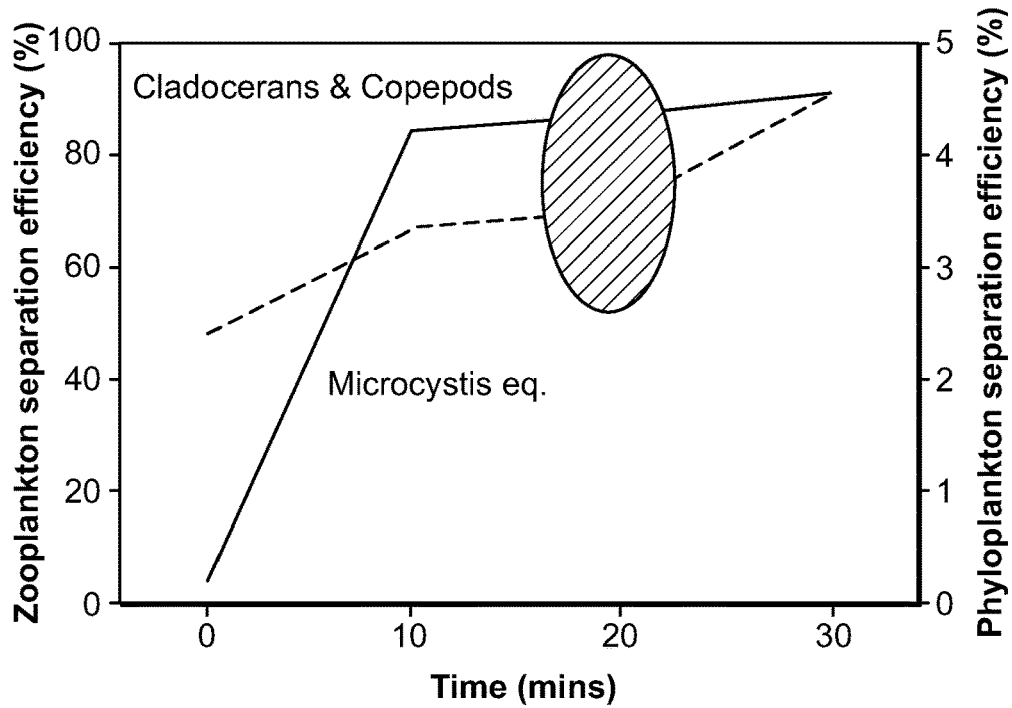
FIG. 5A and FIG. 5B are plots showing calibration curves for macrozooplankton (solid line) and cyanobacteria (dashed line) for Lake Cochichewick (A) and Willand Pond (B) compared with data from Oct. 10 and Oct. 16, 2013, respectively.
Figure 5B:
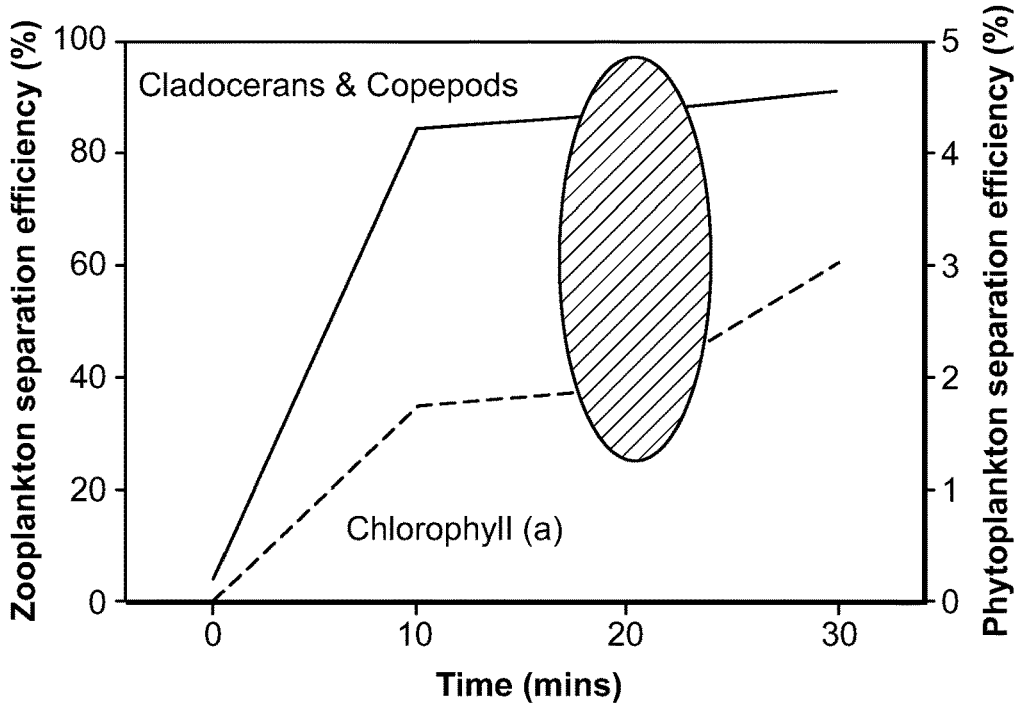
Figure 6:
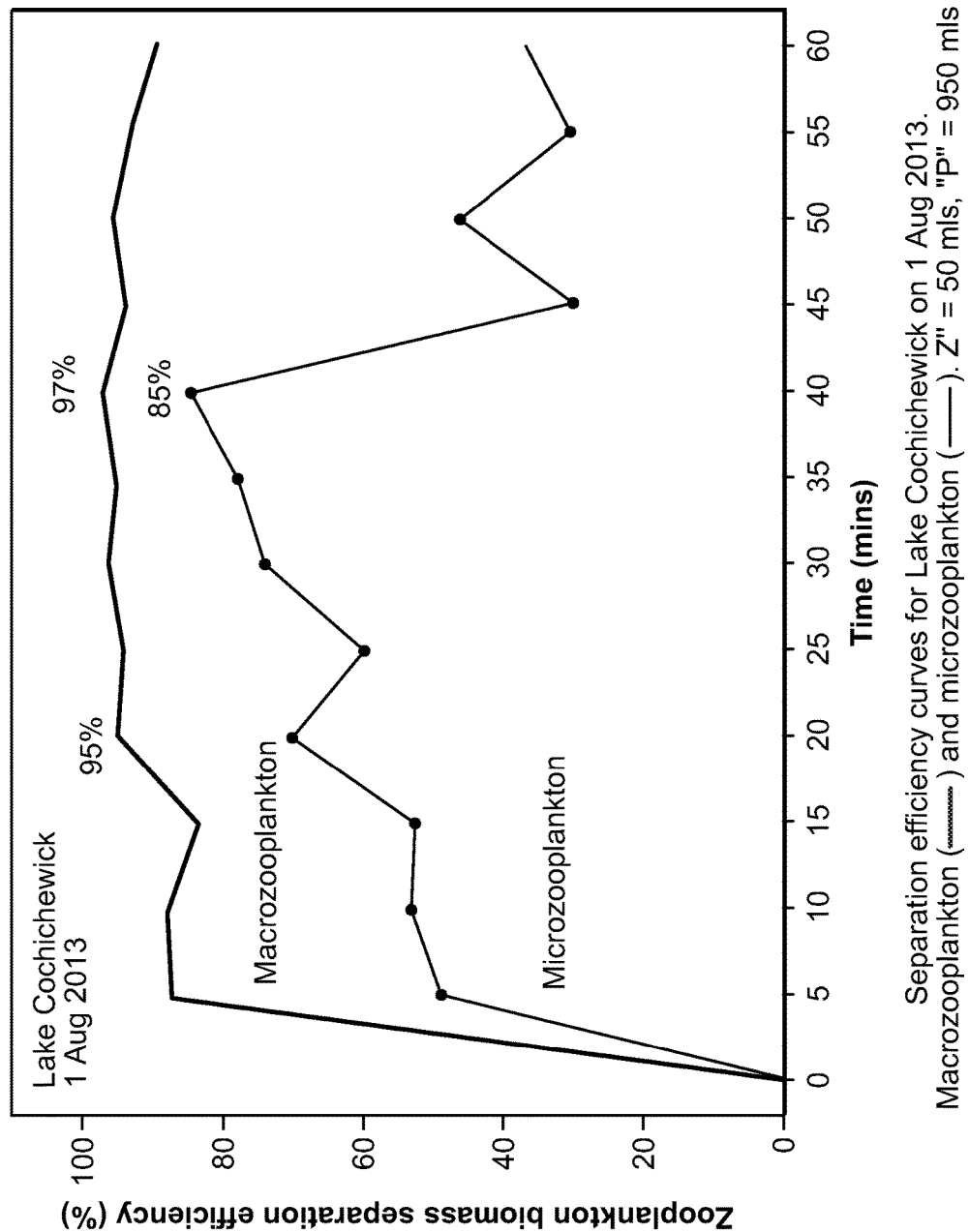
FIG. 6 is a graph showing separation efficiency curves for Lake Cochichewick on Aug. 1, 2013. Macrozooplankton (solid line) and microzooplankton (solid gray line). Z"=50 mls, "P"=950 mls.
Figure 8A:
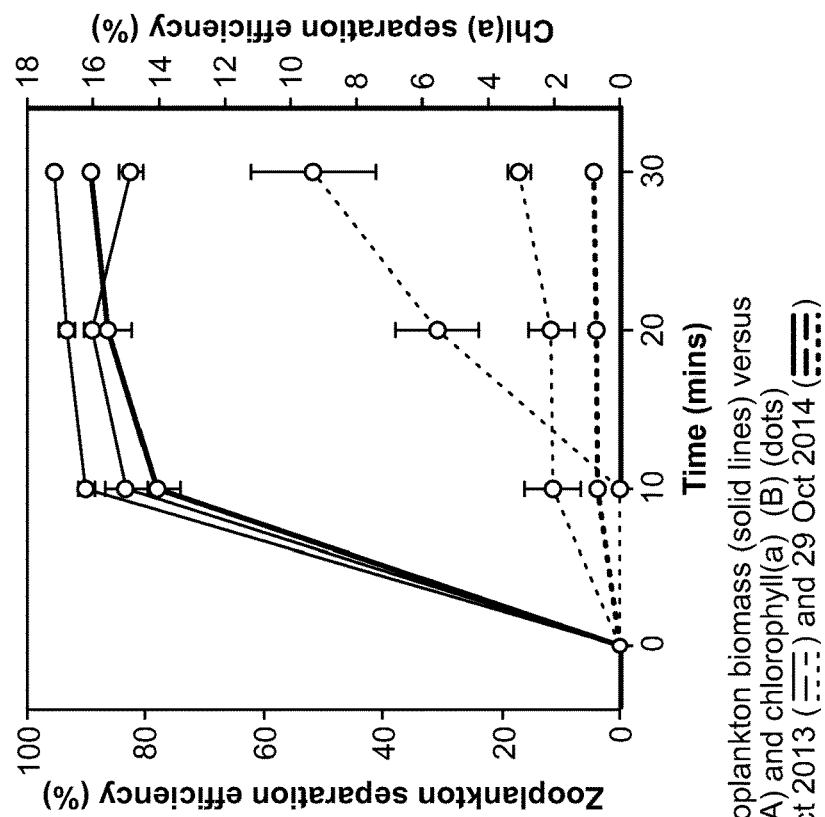
FIGS. 8A and 8B are graphs showing separation efficiency curves for macrozooplankton biomass versus microcystis equivalents and chlorophyll in Lake Cochichewick Sep. 4, 2013, Oct. 10, 2013, and Oct. 29, 2014.
Figure 8B:
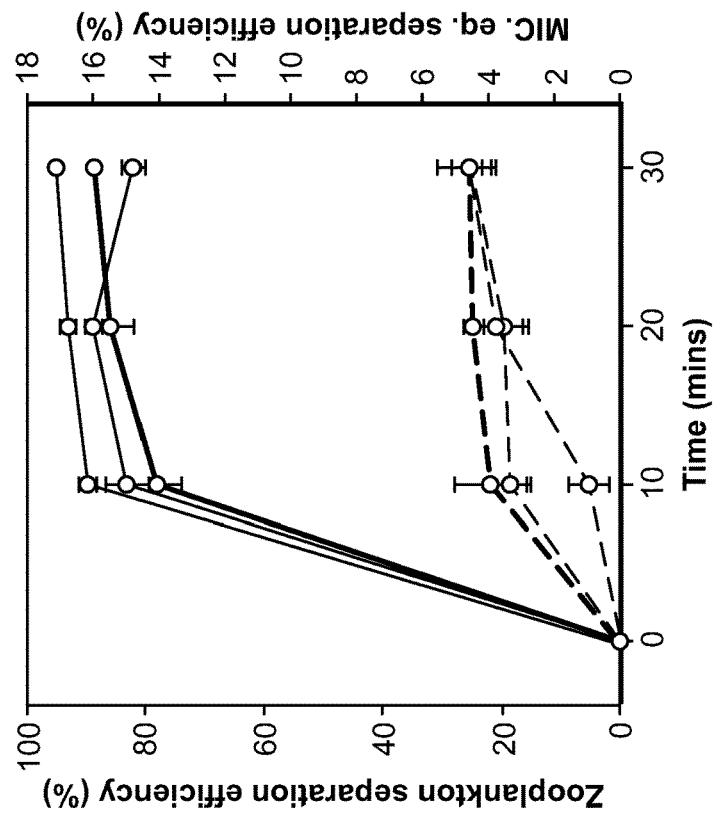
Figures 8C, 8D:
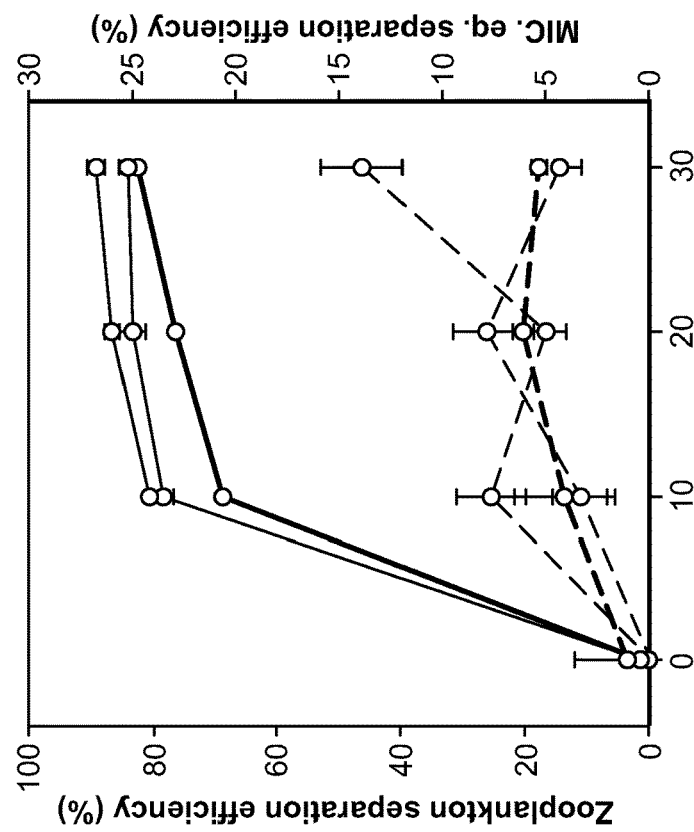
FIGS. 8C and 8D are graphs showing separation efficiency curves for macrozooplankton biomass versus microcystis equivalents and chlorophyll in Willand Pond Sep. 5, 2013, Oct. 16, 2013 and Sep. 6, 2014.

FIG. 5A and FIG. 5B compare the September calibration curves with data from samples taken in October for Lake Cochichewick (FIG. 5A) and Willand Pond (FIG. 5B). The macrozooplankton comprised 93% of the biomass in Lake Cochichewick and 91% of the biomass in Willand Pond.

The calibration curves suggest that the researcher could select a variety of times to allow for the separation of the zooplankton and the phytoplankton depending on project objectives. For this study, the objective was to collect a known volume at a specific time that would contain the greatest biomass of macrozooplankton with the least biomass of cyanobacteria. FIGS. 4A and 4B suggest that, in this context, the researcher should wait 30 minutes before the collection of a 50 ml zooplankton sample, and then collect the remaining 900 mls for a cyanobacterial sample.

Discussion

The results from this study suggest that a rapid method can be used in the field to separate plankton into the component parts. The data suggest that similar results may be obtained when the researcher follows the standard operating procedure and uses a device having design elements sufficient to facilitate a positive phototactic response.

Ambient light was used to simulate the spectral distribution of irradiance in the natural system. Filtered lake water was used to address issues related to dissolved substances and the response of the zooplankton to rapid changes in water temperature.

The design of the separation device with the completely darkened chamber and a transparent collection tube located at a 90 degree vertical position allows for direct illumination which has an angular distribution that approximates 0 (zero).

The design of the separation device with a completely darkened chamber and transparent collection tube provides the conditions to initiate a positive phototactic response to a sudden change in light intensity (Buchanan, C. B. Goldberg and R. McCartney 1982, "A laboratory method for studying zooplankton swimming behaviors," *Hydrobiologic* 94, 77-89). Although measurements of the light intensity were not taken during these experiments, it was assumed that the light intensity exceeds the threshold for instantaneous relative change in light intensity of 0.2 uE m-2 s-1 (the rheobase) necessary for photobehavior to occur. The orientation of the device (darkened above, light below) serves to facilitate and reinforce body axis orientation which results from a response to the spatial change in light intensity (light/dark boundaries, contrast and shadows). *Daphnia magna* have been shown to orient their movements away from overhead shadows as a flight response from predators.

The length of the separation device and the volume of the zooplankton sample to be collected are determined for migration potential and contrast orientation. By creating a sudden stimulus of dark to light to maximize migration rates, the maximum migration distance of 42 cm was achieved within a specified time. Additionally, by leveraging the influence of contrast orientation by driving the zooplankton past the angle of 48° to the normal, optimal conditions were achieved. The optimum volume to be collected using this collection tube was determined to be 50 mls.

In addition to facilitating migration and contrast orientation, the incidental collection of phytoplankton in the zooplankton sample and the zooplankton in the phytoplankton was considered. Optimizing the separation and collection for each portion of the plankton was achieved. Separation efficiency using a method collecting a 50 ml sample versus an alternative method collecting a 250 ml sample demonstrated the superior quality of the samples obtained using the method described herein.

In spite of achieving separation efficiencies that exceeded our expectations, it is still necessary to account for the variability we observed. In regard to the zooplankton, it is possible that the composition and distribution of the biomass had an influence on the separation efficiencies that was observed. It is also possible that lake trophic status exerts a significant influence on separation efficiency. We remain somewhat puzzled at the level of incidental capture of the phytoplankton, specifically the cyanobacteria, in the zooplankton samples and the variability of the results. The calibration curves suggest that after 30 minutes, the levels obtained would be no different than levels obtained from a completely mixed sample. It is unknown whether the incidental capture is from a process of sinking or the combined influence of entrainment and convectional streaming. Since cyanobacteria typically contain gas vacuoles, the phenomenon of sinking does not appear to be the answer.

Example 2

In further examples, data is presented from two separation devices.

Prototype #1 Design Elements:

The device contained design elements as shown in FIG. 1A. The darkened chamber was smooth walled and conical in shape, with a volume of 1 L. The chamber was constructed to prevent light from entering the chamber during the separation phase (tight fitting lid as needed). There was a temporary darkened physical separation between the chamber and collection tube with a diameter of approximately 21.5 mm. This diameter was large enough to allow for a narrow stimulus beam of light to be refracted at an angle approximating 45° (or less) to the vertical plane and to meet the spatial needs of the migrating zooplankton. A stopper was used to provide a temporary physical separation between the chamber and the collection tube. The transparent collection tube allowed for the maximum amount of illumination and was conical in shape to facilitate the collection of zooplankton. The length of the collection tube was such that the zooplankton could migrate past a 45° angle to the vertical plane within the tube. A tube was used with maximum diameter (21.5 mm), minimum diameter (5 mm), length of 150 mm and a maximum volume of 75 mls with rubber tubing (diameter 7 mm) and a clamp. External support to the device was provided via external rings and a sling device.

Prototype #2 Design Elements:

The device contained design elements as shown in FIG. 1D. The design was modified to reduce the variability in separation efficiency and to simplify sample handling. It was assumed there was potential for leakage around the rubber stopper and mixing during its removal, thereby increasing the amount of phytoplankton found in the zooplankton sample. To improve the design, an adapter with a minimum diameter of 20 mm was used as the temporary darkened physical separation. This was a diameter sufficient to allow for a narrow stimulus beam of light to be refracted at an angle approximating 45° (or less) to the vertical plane and to meet the spatial needs of the migrating zooplankton. The conical collection tube, rubber tubing and clamp was replaced with a cylindrical collection cartridge (25 mm diameter) that would continue to meet the spatial needs of the migrating zooplankton and simplify sample handling. Rings were added to provide options for external support.

Collection and Processing of Plankton Samples:

The two study sites included Lake Cochichewick in North Andover, Mass., SA (42°19.7'N: 71°54.9'W) and Willand Pond in Dover, N.H., USA (43°43.1'N: 70°29.6'W). Lake Cochichewick is classified as a mesotrophic system and Willand Pond is classified as an oligotrophic system (Carlson, 1977). The deep sites were accessed by kayak. Concentrated plankton samples were collected between the hours of 10 AM-2 PM using a vertical tow by lowering a 50 um nylon mesh 30 cm open ring conical plankton net fitted with a 50 um mesh bucket to a depth of 5 m (total volume filtered=350 L) and raising vertically at a speed approximating 0.5 m/s. The total number of samples collected depended upon the number of trials to be conducted that day. For example, if 12 trials were to be conducted, 12 samples would be collected. The concentrated plankton samples were placed together in 1 L darkened HDPE (high density polyethylene) bottles. Typically 8-10 concentrated samples would be collected in a single bottle, and 2 bottles of concentrate collected for testing. Whole lake water was collected in 1 L darkened HDPE bottles as a surface grab sample to be used as diluent for the concentrate and as a supply for filtered lake water. The concentrated samples were combined in a 5 L container, mixed, and split using a Folsom plankton splitter until 100 ml aliquots were obtained. The whole lake water (diluent) was combined in a series of 5 L containers and split using a Folsom plankton splitter until 900 ml aliquots were obtained. The individual concentrate portions (100 mls) were combined with the individual diluent portions (900 mls) for a total of 1 L of plankton sample, and placed into 1 L darkened HDPE bottles. Typically, 24 bottles of plankton were prepared in this manner. Filtered lake water was prepared by filtering 1 L of whole lake water through a 50 um mesh ring net and placing it in a 1 L beaker. Prior to use in the separation device, filtered lake water samples were analyzed following Step 3 below.

Plankton Separation—Step 1.

Prototype #1.

The separation device was suspended using a sling apparatus. The collection tube was closed off using the ratchet clamp, and filled with filtered lake water. The collection tube was physically separated from the chamber with the use of a black rubber stopper attached to a plastic rod. The plankton sample was poured into the chamber. The rubber stopper was removed, the lid placed on top of the chamber and the timer set for the desired time interval. When volume series, time series or calibration series were conducted, as many separation devices as needed were prepared in this manner concurrently. For example, when a time series for 0, 10, 20 and 30 minutes was conducted, 4 separation devices were prepared.

Prototype #2.

The collection cartridge was attached to the end of the adapter, filled with filtered lake water and then closed. The plankton sample was placed into the chamber. The adapter/collection tube was screwed onto the chamber, which was then suspended with a sling. The adapter was opened and the timer set for the desired time interval.

Plankton Separation—Step 2.

Prototype #1.

At the desired time interval, the desired volume of sample was released from the collection tube by opening the ratchet clamp, dispensing the sample into a 100 ml sample jar, and then closing the ratchet clamp. This sample was marked as the "Z" (zooplankton) portion. The remainder of the sample was released from the collection tube by opening the ratchet clamp and dispensing the sample into a 1 L carboy. This sample was marked as the "P" (phytoplankton) portion Prototype #2.

At the desired time interval, the adapter was closed and the collection cartridge removed from the bottom of the adapter. The sample was dispensed into a 100 ml sample jar and marked as the "Z" (zooplankton) portion. The chamber was then inverted and the adapter removed. This sample was marked as the "P" (phytoplankton) portion.

Plankton Separation—Step 3.

Phycocyanin (PC) and Chlorophyll (a) (Chla) for the "Z" portion and "P" portion were quantified using a two-channel hand held AquaFluor fluorometer (Turner Designs). Using a disposable pipette 5 mls of each "Z" portion and "P" portion was placed into a 5 ml vial, frozen and then thawed. The thawed sample was placed into a methacrylate cuvette. The filled cuvette was placed in the fluorometer and using channel A, the relative fluorescence units for PC were recorded. Without removing the cuvette from the instrument, channel B was selected and relative fluorescence units for Chla were recorded. PC (excitation at 595 nm, emission at 670 nm) was standardized ($R^2$=0.99, p<0.0000, Microcystis equivalents (MIC eq.)=1369 (x)+4245) using *M. aeruginosa* 2385. Chla (excitation at 460 nm, emission>665 nm) was standardized ($R^2$=0.99, p<0.000, Chla=8624 (x)−120812) with solid secondary standard (No. 8000-952, Turner Designs). The PC and Chla value of the "Z" portion was adjusted (Adj. Z) to account for the background in the filtered water. The MIC eq. and Chla concentrations/ml were adjusted to reflect the volumes collected. The proportion of MIC eq. or Chla (separation efficiency) in the "Z" portion for each sample was calculated as follows:

Adj. MIC eq. "Z"/Adj. MIC eq. "Z"+MIC eq.
"P"=Separation efficiency for cyanobacteria (1)

Adj. Chla "Z"/Adj. Chla "Z"+Chla "P"=Separation
efficiency for phytoplankton (2)

Plankton Separation—Step 4.

The remaining "Z" portion was preserved using 5% formalin/sucrose (Haney & Hall, 1973). The remaining "P" portion was filtered through a 50 um mesh ring net, backwashed with a wash bottle filled with filtered lake water, brought to an appropriate volume using filtered lake water, and preserved using 5% formalin/sucrose.

Plankton Separation—Step 5.

Zooplankton in each "Z" and "P" sample were identified, enumerated and measured using an Amscope T370B-9M compound microscope, a 9.1 megapixel USB 2.0 digital camera, Amscope Version 3.7 digital imaging software and an IBM Think pad. A minimum of 200 individuals were counted in a known subsample volume. The body length (and width as needed) of the first 20 individuals for each genus and/or species was measured. If needed, the count data of the "P" portion was adjusted (Adj. P) to reflect the proportions of sample removed in Step 3 to quantify phycocyanin and Chlorophyll (a). The count data for the "Z" and "P" portion were adjusted to reflect the total sample volume. Dry weight estimates of biomass for cladocerans (*Daphnia* spp., *Diaphanosoma* and *Bosmina*) and copepods and were calculated according to Bottrell (1976). Dry weight estimates of biomass for the cladoceran *Chydorus sphericus*. was calculated according to Dumont (1975). All nauplii were assigned a constant dry weight of 0.40 ug. Dry weight estimates of biomass for rotifers were calculated according to EPA (2003). Values recorded included "Macrozooplankton" and "Microzooplankton". Zooplankton included as "Macrozooplankton" considered the findings of Lampert, W. and B. E. Taylor, 1985, "Zooplankton grazing in a eutrophic lake: Implication of vertical migration," *Ecology* 66:68-92, Lampert, W., W. Fleckner, H. Rai and B. E. Taylor, 1986, "Phytoplankton control by grazing zooplankton: A study on the spring clear-water phase," *Limnol. Oceanogr.* 31(3): 478-490, Watras, C. J. and N. Bloom, 1992, "Mercury and methylmercury in individual zooplankton: Implications for bioaccumulation," *Limnol. Oceanogr.*, 37(6):1313-1318, and Back, R. C., V. Visman, and C. J. Watras, 1995, "Microhomogenization of individual zooplankton species improves mercury and methylmercury determinations," *Can. J. Fish. Aquat. Sci.*, 52: 2470-2475 and included any genus and/or species which comprised greater than 1.0% of the total biomass of the sample.

The zooplankton biomass separation efficiency for each sample was calculated as follows:

Dry wt. "Z"/Dry wt."Z"+Dry wt. Adj.
"P"=Zooplankton biomass separation efficiency (3)

All proportionate values were arcsine transformed (Zar, Jerrold H., "Biostatistical Analysis," Prentice-Hall, Inc. New Jersey. 1974 ed.). Studentized T-tests and analysis of variance (ANOVA) were conducted using SigmaPlot V. 12.5.

Assessment

An experiment in Lake Cochichewick (1 Aug. 2013) using prototype #1 was designed to evaluate separation efficiencies for zooplankton using the methods described in Steps 1-2 and Steps 4-5. Separation efficiency curves as shown in FIG. 2 indicate that the maximum separation efficiency occurred at T=40 minutes for Macrozooplankton (97%) and Microzooplankton (85%). Separation efficiencies greater than 90% occurred at T=20 minutes for Macrozooplankton (95%).

The experimental design was modified to evaluate separation efficiencies for zooplankton and phytoplankton using the methods described in Steps 1-5. This would allow determination of the optimal separation time that would provide samples with the greatest amount of zooplankton biomass (with minimal phytoplankton) and phytoplankton biomass (with minimal zooplankton). Experiments were conducted using samples from Lake Cochichewick (4 Sep. 2013, 10 Oct. 2013) and Willand Pond (5 Sep. 2013, 16 Oct. 2013). FIGS. 7A and 7B show the separations for macrozooplankton, microcystis equivalents and chlorophyll(a) for Lake Cochichewick. The mean values for macrozooplankton ranged between 90-95% (September) and 82-89% (October). The mean values for microcystis equivalents ranged between 3-5% (September) and 1-5% (October), while the chlorophyll(a) values ranged from 2-3% (September) and 6-9% (October). The macrozooplankton found in Lake Cochichewick in September and October included *Diaphanosoma brachyurum*, *Diaptomus* spp. and *Microcyclops rubellus*. FIGS. 7C and 7D show the separations for macrozooplankton, microcystis equivalents and chlorophyll(a) for Willand Pond. The mean values for macrozooplankton ranged between 81-89% (September) and 79-84% (October). The mean values for microcystis equivalents ranged between 3-8% (September) and 5-14% (October), while the chlorophyll(a) values ranged from 3-11% (September) and 6-17% (October). The macrozooplankton found in Willand Pond in September and October included *Daphnia ambigua, Daphnia catawba, Diaptomus* spp. and *Mesocyclops edax*.

The experiments were repeated for Lake Cochichewick (29 Oct. 2014) and Willand Pond (6 Sep. 2014) using prototype #2. FIGS. 8A, 8B, 8C and 8D offer a comparison of the 2013 and 2014 experiments. In Lake Cochichewick, separation efficiencies for macrozooplankton (78-89%), microcystis equivalents (4-5%) and chlorophyll(a) (4%) were observed. In Willand Pond, separation efficiencies for macrozooplankton (69-83%), microcystis equivalents (4-6%) and chlorophyll(a) (3%) were observed. Two additional macrozooplankton were found in Lake Cochichewick in 2014, including *Daphnia ambigua* and *Daphnia mendotae*, while the macrozooplankton found in Willand Pond remained unchanged. The experiments confirmed that objectives have met to reduce the variability in separation efficiency with an improved design of the device. Analysis of variance revealed that the zooplankton separation efficiencies were not significantly different from 2013 to 2014 for either lake. In Lake Cochichewick, the amount of chlorophyll(a) was significantly reduced at T=20 minutes (p=0.024) and T=30 minutes (p=0.049). In Willand Pond, the amount of microcystis equivalents was significantly reduced at T=30 minutes (p=0.018) and the amount of chlorophyll(a) was significantly reduced at T=20 minutes (p=0.009). The reduction in the variability of the data was evidenced by the decrease in the standard deviation for the microcystis equivalents and chlorophyll(a) values from 2013 to 2014.

Figure 9:
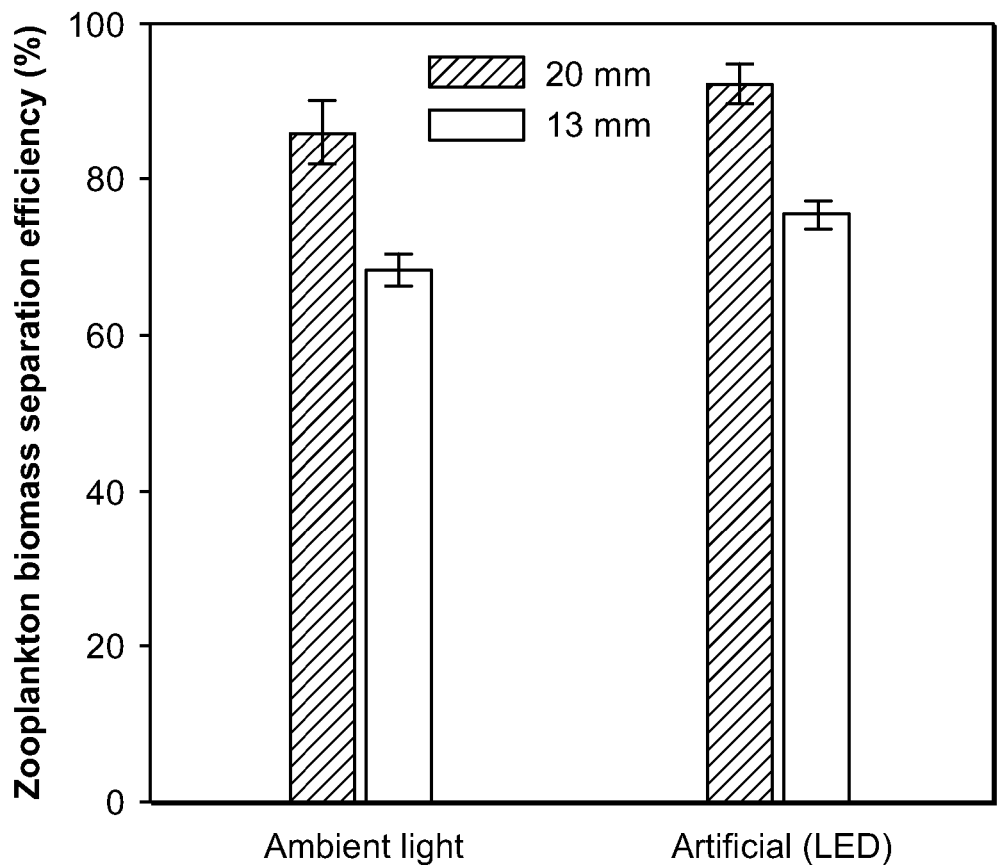
FIG. 9 is a graph depicting effect of minimum adapter diameter on separation efficiency. Macrozooplankton in Lake Cochichewick 29 Oct. 2014 with standard errors for each shown. Ambient (t-3.54, df-4, p-0.024), Artificial (t-4.90, df-4, p-0.008).

FIG. 9 provides evidence as to the importance of the spatial needs of the migrating zooplankton. This experiment evaluated the effect of the minimum diameter of the adapter that provided the temporary darkened physical separation. The experiments were conducted with ambient and artificial light, as well as adapters with minimum diameters of 20 mm and 13 mm. During the experiments with the 20 mm adapter, it was noted that the animals migrated freely, appearing in the collection cartridge within a minute of opening the ball valve. However, when the 13 mm adapter was used, 2 of the 3 collection cartridges did not have any zooplankton in them after as many as 5 minutes. The cartridges needed to be gently tapped to release the animals that were apparently clogging the opening. T-tests revealed that there was no significant difference in separation efficiency when using ambient light or artificial (LED) light for either the 20 mm or 13 mm adapter. However, the separation efficiency for the 20 mm adapter was significantly higher than the 13 mm adapter under ambient (t=3.54, df=4, p=0.024) and artificial (t=4.90, df=4, p=0.008) illumination.

Figure 10:
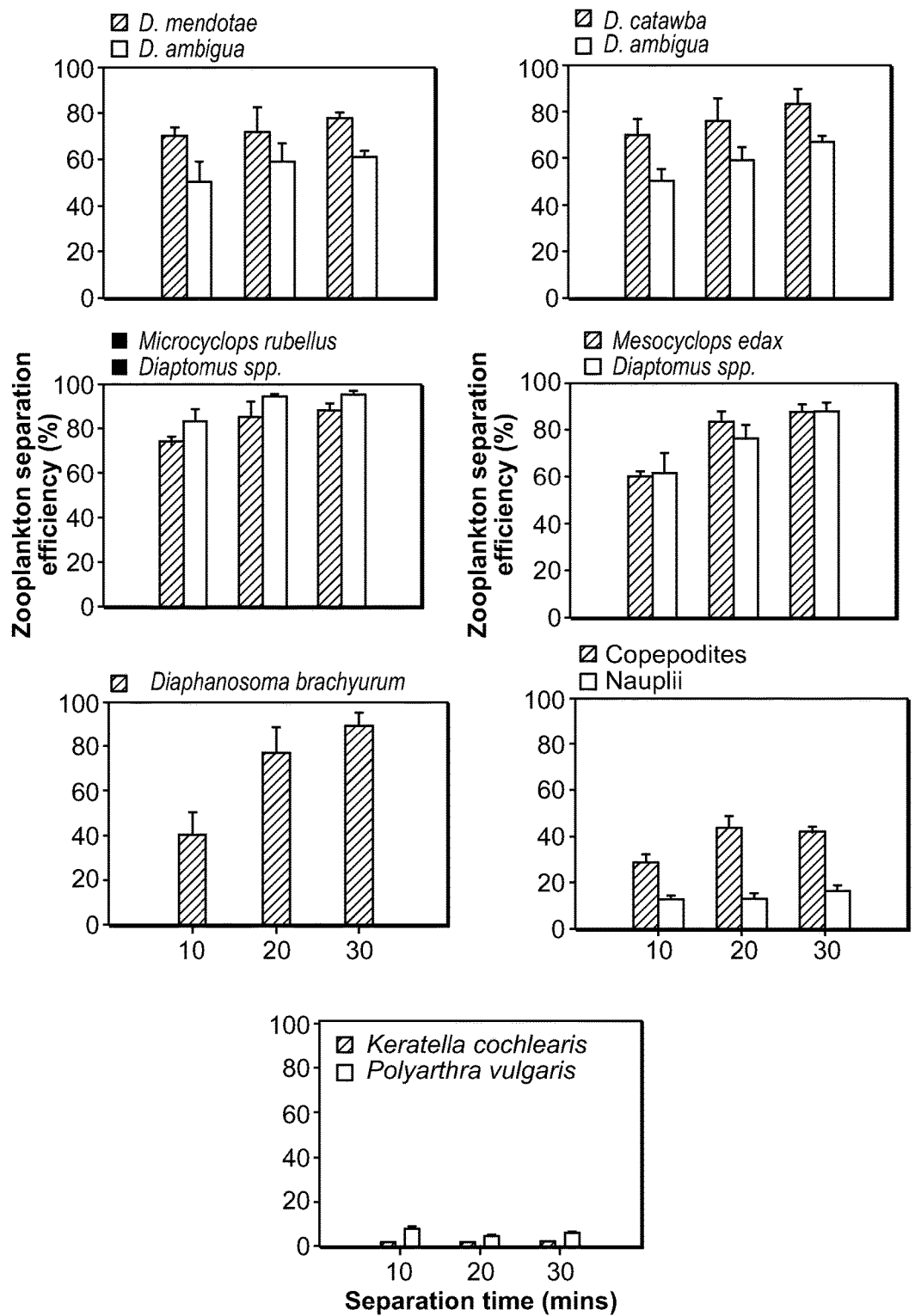
FIG. 10 are graphs showing separation efficiencies for individual zooplankters from Lake Cochichewick on Oct. 29, 2014 and Willand Pond on Sep. 6, 2014.

The separation efficiencies provide greater insights into the phototactic behavior, under these conditions, of an in-situ zooplankton community taken from two distinct waterbodies. Although there was some overlap in the zooplankton community composition between the two lakes (e.g., *D. ambigua, Diaptomus* spp, copepodites, nauplii), there were distinct genus and species as well (e.g., *D. catawba, D. mendotae, Diaphanosoma brachyurum, Microcyclops rubellus* and *Mesocyclops edax*.). Community composition and distribution could ultimately influence the separation efficiencies that could be achieved for any given waterbody. Additionally, knowledge of the separation efficiencies of the individual zooplankters could potentially allow for the selection of a separation time based upon a target organism. FIG. 10 provides a summary of the individual zooplankter behavior that was observed in samples taken from Lake Cochichewick and Willand Pond in 2014. These are comparable to those previously observed as shown in Table 1 of FIG. 11 and Table 2 of FIG. 12, respectively.

The design of the separation device with a completely darkened chamber and transparent collection tube provides the conditions necessary to initiate a positive phototactic response to a sudden change in light intensity (Buchanan, C. B. Goldberg and R. McCartney, 1982, "A laboratory method for studying zooplankton swimming behaviors," *Hydrobiologic*, 94, 77-89). Although the light intensity was not measured during these experiments, it was assumed that the light intensity exceeded the threshold for instantaneous relative change in light intensity of 0.2 uE m−2 s−1 (the rheobase) necessary for photobehavior to occur (Ringelberg, J., 1964, "The positively phototactic reaction of *Daphnia magna* Straus: a contribution to the understanding of diurnal vertical migration," *Neth. J. Sea Res.*, 2:319-406, Daan, N. and J. Ringelberg, 1969, "Further studies on the positive and negative phototactic reaction of *Daphnia magna* Straus," *Neth. J. Zool.*, 19:525-540). A positive phototactic response could be anticipated as a result of exposure to a narrow stimulus beam (Forward, R. B. Jr., 1988, "Diel vertical migration: Zooplankton photobiology and behavior," *Oceanogr. Mar. Biol. Annu. Rev.*, 26: 361-393) (highly directional light) with an angular light distribution that approximates 0° (Schallek, W., 1942, "The vertical migration of the copepod *Acartia tonsa* under controlled illumination," *Biological Bulletin,* 84:98-106). Body axis orientation would result from dorsal beam contrast (45° or less) (Ringelberg, J., 1964, "The positively phototactic reaction of *Daphnia magna* Straus: a contribution to the understanding of diurnal vertical migration," *Neth. J. Sea Res.* 2:319-406) (Ringelberg, J., B. J. G. Flik and R. C. Buis, 1975, "Contrast orientation in *Daphnia magna* and its significance for vertical plane orientation in the pelagic biotope in general," *Neth. J. Zool.,* 25:454-475) that would control the direction of movement in the vertical plane. The orientation of the device (darkened above, light below) serves to reinforce body axis orientation as a flight response from predators.

An adapter with a minimum diameter of 20 mm was used as the temporary darkened physical separation. This was a diameter sufficient to allow for a narrow stimulus beam of light to be refracted at an angle approximating 45° (or less) to the vertical plane and to meet the spatial needs of the migrating zooplankton. A cylindrical collection tube (25 mm diameter) continuously assured that the spatial needs of the migrating zooplankton would be met. Although experiments were not conducted on the behavior of the migrating zooplankton in devices with other elements (i.e., rubber tubing) with small diameter (e.g., 13 mm or less), it is assumed that the response would be similar. Consequently, it is possible that elements of a separation device with diameters less than 13 mm may inhibit the movement of migrating zooplankton.

The volume of the zooplankton sample to be collected needed to consider migration potential and contrast orientation. By creating a sudden stimulus of dark to light to maximize migration rates, (Buchanan, Goldberg and McCartney 1982) it could be ensured that the maximum migration distance of 42 cms could be achieved within a specified time (Daan & Ringelberg 1969). Additionally, it was needed to leverage the influence of contrast orientation by driving the zooplankton past the angle of 48° to the normal. The optimum volume to be collected using a collection tube was determined to be 50 mls.

In regards to procedural issues, favorable conditions were established for the response to occur by using ambient light to simulate the spectral distribution of irradiance in the natural system. Filtered lake water was used to address issues related to dissolved substances and response of the zooplankton to rapid changes in water temperature. (Buchanan, Goldberg and McCartney, 1982).

The device is easily assembled and can be used to obtain well separated in situ samples of phytoplankton and zooplankton. The samples can easily be processed on site, thereby reducing valuable time either in the field or in the laboratory. Issues related to sample handling and transport were considered, and how that might affect the design of the collection tubes. Collection tubes containing samples of live zooplankton can be sealed with a cap and easily transported. The phytoplankton can be easily transported by placing a cap on the darkened chamber. To simplify transport and reduce processing time in the lab, dried zooplankton and phytoplankton samples can be obtained while in the field. This would also reduce the possibility of bacterial contaminations of the samples. Filter cones and modified collection tubes were developed to allow for the discharge of water. The filter cones can be placed in drying chambers for 2-8 hours and then placed into desiccators. There are competing limitations to the device and the method that relate to a vacuum being created within the chamber and incremental clogging of the filter cone as the phytoplankton sample is being discharged. These limitation can be overcome by the sizing of the filter cones and including agitation ports in the collection tubes.

Discussion:

The experiments described herein provide novel data, using an in situ sample to quantify phototactic behavior under a controlled setting from two distinctly different water bodies. Although phototaxis has been previously used to separate plankton, there are no published studies that describe the actual separation efficiencies that could be achieved. From visual observations, phototactic behavior can be used to harvest zooplankton. The composition of the sample was unknown, however it was assumed that macrozooplankton would migrate more quickly than microzooplankton. Additionally, the amount of incidental capture of the phytoplankton portion was completely unknown. The harvest achieved for the zooplankton portion surpassed expectations and provided insight into the level of incidental phytoplankton capture that could be anticipated. Conversely, a phytoplankton portion can be harvested that would be relatively free of zooplankton biomass. The passive nature of the device proved to be of great value, as other tasks could be conducted while the sample was separating, thereby saving valuable time.

In regards to the zooplankton, it is possible that the composition and distribution of the biomass had an influence on the separation efficiencies that were observed. It is also possible that lake trophic status exerts a significant influence on separation efficiency. The level (5% or less) of incidental capture of the phytoplankton is puzzling, specifically the cyanobacteria, in the zooplankton samples. It is assumed that what is observed as incidental capture is a result of depuration as the zooplankton move from an environment of high concentration of phytoplankton to a lower concentration.

It is anticipated that samples obtained after using the method and device would yield relatively precise measures of biomass and weight specific toxicity for zooplankton and phytoplankton. The phytoplankton information could be used to provide a profile of exposure potential across a range of waterbodies and to support decisions regarding use attainability. The zooplankton information could be used to quantify transfer between the two trophic levels and provide insight into the potential for further bioaccumulation.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for separating plankton, comprising:
   placing a plankton sample comprising zooplankton and phytoplankton in a darkened chamber, wherein the darkened chamber has an outer perimeter surrounding a vertical central axis, and a maximum outer perimeter dimension that extends downwardly to a darkened narrowed section, wherein the darkened narrowed section has an inner opening having a size above 13 mm and up to 21.5 mm±2 mm;
   acclimating the plankton for a sufficient amount of time to facilitate a response by the zooplankton to a change in light intensity; and
   introducing ambient light to the chamber to initiate phototactic movement of the zooplankton to a collection tube filled with water, the phototactic movement into the collection tube separating the zooplankton from the phytoplankton, wherein the collection tube is of sufficient length to reinforce contrast orientation and is a light permeable collection tube extending along the vertical central axis attached to the darkened narrowed section for allowing highly directional ambient light to enter the collection tube and pass upwardly through the darkened narrowed section and inner opening which are configured to produce a narrow defined beam of light upwardly into the darkened chamber along the vertical central axis without inhibiting zooplankton migration therethrough, wherein the collection tube is of sufficient length to reinforce migration of the zooplankton downwardly, by extending downwardly away from the darkened chamber beyond a point that makes about a 20°±2° angle to the vertical central axis while extending to a nearest location of maximum outer perimeter dimension of the darkened chamber, thereby providing a contrast shadow from the darkened chamber relative to the collection tube simulating a predator to zooplankton, and a length in the collection tube for zooplankton to migrate from and move away from the darkened chamber a sufficient distance to minimize zooplankton collected in the collection tube from migrating back into the darkened chamber, thereby separating plankton into its component parts.

2. The method of claim 1, wherein the plankton are acclimated for 20 minutes or less.

3. The method of claim 1, wherein the collection tube is transparent.

4. The method of claim 1 wherein the collection tube is located below the darkened chamber at a 90° angle relative to a horizontal base of the darkened chamber.

5. The method of claim 1, wherein the collection tube has a length sufficient to ensure that an angle of 48° relative to the vertical central axis and a line extending from a point along the vertical central axis that intersects with the maximum outer perimeter dimension is above to normal can be achieved by the zooplankton in the collection tube.

6. The device of claim 1, wherein the darkened chamber has a port, the collection tube being connected to the port.

7. The method of claim 6, wherein the port has a closure, the closure being changeable from a closed state to an open state.

8. The method of claim 3, wherein the darkened chamber and the collection tube have outer diameters with a darkened chamber $OD_b$ to transparent collection tube $OD_t$ ratio of about 3-3.5 to 1, the transparent collection tube having a length with a transparent collection tube length to $OD_t$ ratio of about 3.9-5.2 to 1, thereby providing a contrast shadow relative to the transparent collection tube simulating a predator to plankton, and sufficient length in the transparent collection tube for plankton to migrate from and move away from the darkened chamber to minimize plankton collected in the transparent collection tube from migrating back into the darkened chamber.

9. The method of claim 1 in which the inner opening from the darkened chamber into the collection tube is in the range of about 19 to about 22 mm across.

10. The method of claim 1, wherein the plankton are separated for about 30 minutes.

11. A plankton separation method comprising:
introducing a plankton sample comprising zooplankton and phytoplankton to a darkened chamber of a plankton separating device comprising:
a darkened chamber having a port, wherein the darkened chamber has an outer perimeter surrounding a vertical central axis, and a maximum outer perimeter dimension that extends downwardly to a darkened narrowed section, wherein the darkened narrowed section has an inner opening having a size above 13 mm and up to 21.5 mm±2 mm; and
a collection tube attached to the port of the chamber for allowing highly directional ambient light, wherein the collection tube is of sufficient length to reinforce migration of the zooplankton and is a light permeable collection tube extending along the vertical central axis attached to the darkened narrowed section for allowing highly directional ambient light to enter the collection tube and pass upwardly through the darkened narrowed section and inner opening which are configured to produce a narrow defined beam of light upwardly into the darkened chamber along the vertical central axis without inhibiting zooplankton migration therethrough, wherein the collection tube is of sufficient length to reinforce migration of the zooplankton downwardly, by extending downwardly away from the darkened chamber beyond a point that makes about a 20°±2° angle to the vertical central axis while extending to a nearest location of maximum outer perimeter dimension of the darkened chamber, thereby providing a contrast shadow from the darkened chamber relative to the collection tube simulating a predator to zooplankton, and a length in the collection tube for zooplankton to migrate from and move away from the darkened chamber a sufficient distance to minimize zooplankton collected in the collection tube from migrating back into the darkened chamber, thereby separating plankton into its component parts,
acclimating the sample for a sufficient amount of time to facilitate a response to a sudden change in light intensity,
introducing highly directional ambient light at a sufficient level to initiate phototactic movement to the collection tube filled with water, said tube of sufficient length to reinforce negative contrast orientation, wherein the zooplankton is separated from the phytoplankton,
collecting zooplankton from the collection tube; and
collecting phytoplankton from the collection tube, wherein the plankton is separated to zooplankton and phytoplankton samples.

12. The method of claim 11, wherein the port has a closure configured to be changed from a closed state to an open state with the collection tube attached to the port.

13. A method for separating plankton, comprising:
placing a plankton sample comprising zooplankton and phytoplankton in a darkened chamber of a plankton separation device, the darkened chamber having an outer perimeter surrounding a vertical central axis, and a maximum outer perimeter dimension that extends downwardly to a darkened narrowed section, wherein the darkened narrowed section has an inner opening having a size above 13 mm and up to 21.5 mm±2 mm; and
allowing light to enter a light permeable collection tube extending along the vertical central axis and extending from the darkened narrowed section, the light passing upwardly through the darkened narrowed section and inner opening, which are configured to produce a narrow defined beam of light into the darkened chamber along the vertical central axis without inhibiting zooplankton migration therethrough, the collection tube of sufficient length to reinforce migration of zooplankton downwardly, by extending downwardly away from the darkened chamber beyond a point that makes about a 20°±2° angle to the vertical central axis while extending to a nearest location of maximum outer perimeter dimension of the darkened chamber, thereby providing a contrast shadow relative to the collection tube simulating a predator to zooplankton, and sufficient length in the collection tube for zooplankton to migrate from and move away from the darkened chamber a sufficient distance to minimize zooplankton collected in the collection tube from migrating back into the darkened chamber.

14. A method for separating plankton, comprising:

placing a plankton sample comprising zooplankton and phytoplankton in a darkened chamber;

acclimating the plankton for a sufficient amount of time to facilitate a response by the zooplankton to a change in light intensity; and introducing ambient light to the chamber to initiate phototactic movement of the zooplankton to a transparent collection tube filled with water, the phototactic movement into the collection tube separating the zooplankton from the phytoplankton, and wherein the darkened chamber and the collection tube have outer diameters with a darkened chamber $OD_b$ to transparent collection tube $OD_t$ ratio of about 3-3.5 to 1, the transparent collection tube having a length with a transparent collection tube length to $OD_t$ ratio of about 3.9-5.2 to 1, thereby providing a contrast shadow relative to the transparent collection tube simulating a predator to plankton, and sufficient length in the transparent collection tube for plankton to migrate from and move away from the darkened chamber to minimize plankton collected in the transparent collection tube from migrating back into the darkened chamber.

* * * * *

UNITED STATES PATENT AND TRADEMARK OFFICE
CERTIFICATE OF CORRECTION

PATENT NO. : 10,227,580 B2
APPLICATION NO. : 15/345823
DATED : March 12, 2019
INVENTOR(S) : Nancy Leland Page 1 of 1

It is certified that error appears in the above-identified patent and that said Letters Patent is hereby corrected as shown below:

In the Claims

In Claim 5, Column 27, Lines 37-38, delete "to normal can be achieved by"

Signed and Sealed this
Seventh Day of May, 2019

Andrei Iancu
*Director of the United States Patent and Trademark Office*